United States Patent
Aguirre et al.

(10) Patent No.: US 12,337,320 B2
(45) Date of Patent: Jun. 24, 2025

(54) SYSTEMS AND METHODS FOR PARTICLE FOCUSING IN MICROCHANNELS

(71) Applicant: ABS Global, Inc., DeForest, WI (US)

(72) Inventors: Gerson Aguirre, Seattle, WA (US); Zheng Xia, DeForest, WI (US); Gopakumar Kamalakshakurup, DeForest, WI (US)

(73) Assignee: ABS GLOBAL, INC., Deforest, WI (US)

( * ) Notice: Subject to any disclaimer, the term of this patent is extended or adjusted under 35 U.S.C. 154(b) by 665 days.

(21) Appl. No.: 17/714,020

(22) Filed: Apr. 5, 2022

(65) Prior Publication Data

US 2022/0226827 A1 Jul. 21, 2022

Related U.S. Application Data

(63) Continuation of application No. 16/419,756, filed on May 22, 2019, now Pat. No. 11,331,670.

(60) Provisional application No. 62/675,512, filed on May 23, 2018.

(51) Int. Cl.
 *B01L 3/00* (2006.01)
(52) U.S. Cl.
 CPC . *B01L 3/502761* (2013.01); *B01L 2200/0652* (2013.01); *B01L 2300/0883* (2013.01); *B01L 2400/086* (2013.01)
(58) Field of Classification Search
 CPC ....... B01L 3/502761; B01L 2200/0652; B01L 2300/0883; B01L 2400/086
 See application file for complete search history.

(56) References Cited

U.S. PATENT DOCUMENTS

| | | | |
|---|---|---|---|
| 3,390,449 A | 7/1968 | Fox | |
| 3,649,829 A | 3/1972 | Randolph | |
| 3,661,460 A | 5/1972 | Elking et al. | |
| 3,710,933 A | 1/1973 | Fulwyler et al. | |
| 3,764,901 A | 10/1973 | Kachel | |
| 3,791,517 A | 2/1974 | Friedman | |
| 4,175,662 A | 11/1979 | Zold | |
| 4,325,706 A | 4/1982 | Gershman et al. | |
| 4,395,397 A | 7/1983 | Shapiro | |

(Continued)

FOREIGN PATENT DOCUMENTS

| | | |
|---|---|---|
| CA | 1341328 C | 12/2001 |
| CN | 2125369 U | 12/1992 |

(Continued)

OTHER PUBLICATIONS

Sell, "Cellular Origin of Cancer: Dedifferentiation or Stem Cell Maturation Arrest?", Environmental Health Perspectives, vol. 101, Suppl. 5, 1993, p. 15-26.

(Continued)

*Primary Examiner* — Brian J. Sines
(74) *Attorney, Agent, or Firm* — NGUYEN TARBET IP LAW

(57) ABSTRACT

A microfluidic system configured to focus particles suspended in a fluid. One general aspect includes a microfluidic system comprising one or more substrates and a focusing channel formed in the one or more substrates and spanning a length from an inlet to an outlet for receiving a flow of particles suspended in fluid, wherein the particles have a diameter (a) and the focusing channel has a hydraulic diameter (dh).

26 Claims, 4 Drawing Sheets

(56) References Cited

U.S. PATENT DOCUMENTS

| | | |
|---|---|---|
| 4,409,106 A | 10/1983 | Furuta et al. |
| 4,424,132 A | 1/1984 | Iriguchi |
| 4,660,971 A | 4/1987 | Sage et al. |
| 4,667,830 A | 5/1987 | Nozaki, Jr. et al. |
| 4,765,737 A | 8/1988 | Harris et al. |
| 4,885,473 A | 12/1989 | Shofner et al. |
| 4,919,817 A | 4/1990 | Schoendorfer et al. |
| 4,983,038 A | 1/1991 | Ohki et al. |
| 5,007,732 A | 4/1991 | Ohki et al. |
| 5,030,002 A | 7/1991 | North, Jr. |
| 5,100,627 A | 3/1992 | Buican et al. |
| 5,125,749 A | 6/1992 | Leugers et al. |
| 5,135,759 A | 8/1992 | Johnson |
| 5,180,065 A | 1/1993 | Touge et al. |
| 5,194,909 A | 3/1993 | Tycko |
| 5,229,297 A | 7/1993 | Schnipelsky et al. |
| 5,483,469 A | 1/1996 | Van den Engh et al. |
| 5,491,550 A | 2/1996 | Dabbs |
| 5,620,857 A | 4/1997 | Weetall et al. |
| 5,674,743 A | 10/1997 | Ulmer |
| 5,689,109 A | 11/1997 | Schütze |
| 5,752,606 A | 5/1998 | Wilson et al. |
| 5,800,690 A | 9/1998 | Chow et al. |
| 5,837,115 A | 11/1998 | Austin et al. |
| 5,849,178 A | 12/1998 | Holm et al. |
| 5,858,187 A | 1/1999 | Ramsey et al. |
| 5,879,625 A | 3/1999 | Rosianiec et al. |
| 5,966,457 A | 10/1999 | Lemelson |
| 5,976,885 A | 11/1999 | Cohenford |
| 5,985,216 A | 11/1999 | Rens et al. |
| 6,008,010 A | 12/1999 | Greenberger et al. |
| 6,053,856 A | 4/2000 | Hlavinka |
| 6,071,442 A | 6/2000 | Dean et al. |
| 6,146,897 A | 11/2000 | Cohenford et al. |
| 6,159,739 A | 12/2000 | Weigl et al. |
| 6,159,749 A | 12/2000 | Liu |
| 6,171,865 B1 | 1/2001 | Weigl et al. |
| 6,185,664 B1 | 2/2001 | Jeddeloh |
| 6,213,151 B1 | 4/2001 | Jacobson et al. |
| H1960 H | 6/2001 | Conrad et al. |
| 6,368,871 B1 | 4/2002 | Christel et al. |
| 6,416,190 B1 | 7/2002 | Grier et al. |
| 6,416,959 B1 | 7/2002 | Giuliano et al. |
| 6,432,630 B1 | 8/2002 | Blankenstein |
| 6,451,264 B1 | 9/2002 | Bhullar et al. |
| 6,473,171 B1 | 10/2002 | Buttry et al. |
| 6,494,230 B2 | 12/2002 | Chow |
| 6,506,609 B1 | 1/2003 | Wada |
| 6,519,032 B1 | 2/2003 | Kuebler et al. |
| 6,519,954 B1 | 2/2003 | Prien et al. |
| 6,524,860 B1 | 2/2003 | Seidel et al. |
| 6,540,895 B1 | 4/2003 | Spence et al. |
| 6,549,275 B1 | 4/2003 | Cabuz et al. |
| 6,592,821 B1 | 7/2003 | Wada et al. |
| 6,637,463 B1 | 10/2003 | Lei et al. |
| 6,674,525 B2 | 1/2004 | Bardell et al. |
| 6,727,451 B1 | 4/2004 | Fuhr et al. |
| 6,808,075 B2 | 10/2004 | Böhm et al. |
| 6,833,542 B2 | 12/2004 | Wang et al. |
| 6,838,056 B2 | 1/2005 | Foster |
| 6,841,388 B2 | 1/2005 | Dukor et al. |
| 6,853,654 B2 | 2/2005 | Mcdonald et al. |
| 6,877,528 B2 | 4/2005 | Gilbert et al. |
| 6,944,324 B2 | 9/2005 | Tran et al. |
| 6,976,590 B2 | 12/2005 | Deshpande et al. |
| 7,029,430 B2 | 4/2006 | Hlavinka et al. |
| 7,069,943 B2 | 7/2006 | Gilbert et al. |
| 7,092,154 B2 | 8/2006 | Yasuda et al. |
| 7,104,405 B2 | 9/2006 | Böhm et al. |
| 7,195,920 B2 | 3/2007 | Seidel et al. |
| 7,208,265 B1 | 4/2007 | Schenk |
| 7,241,988 B2 | 7/2007 | Gruber et al. |
| 7,276,701 B2 | 10/2007 | Lendl |
| 7,298,478 B2 | 11/2007 | Gilbert et al. |
| 7,300,803 B2 | 11/2007 | Lin et al. |
| 7,311,476 B2 | 12/2007 | Gilbert et al. |
| 7,312,085 B2 | 12/2007 | Chou et al. |
| 7,355,696 B2 | 4/2008 | Mueth et al. |
| 7,355,699 B2 | 4/2008 | Gilbert et al. |
| 7,466,734 B1 | 12/2008 | Day et al. |
| 7,472,794 B2 | 1/2009 | Oakey et al. |
| 7,482,577 B2 | 1/2009 | Gruber et al. |
| 7,492,522 B2 | 2/2009 | Gilbert et al. |
| 7,524,681 B2 | 4/2009 | Wolf et al. |
| 7,569,788 B2 | 8/2009 | Deshpande et al. |
| 7,576,861 B2 | 8/2009 | Gilbert et al. |
| 7,584,857 B2 | 9/2009 | Böhm et al. |
| 7,611,309 B2 | 11/2009 | Gilbert et al. |
| 7,670,471 B2 | 3/2010 | Quake et al. |
| 7,697,576 B2 | 4/2010 | Maier et al. |
| 7,758,811 B2 | 7/2010 | Durack et al. |
| 7,760,351 B2 | 7/2010 | Cox et al. |
| 7,820,425 B2 | 10/2010 | Schenk |
| 7,826,509 B2 | 11/2010 | Belkin et al. |
| 7,956,328 B2 | 6/2011 | Sundaram et al. |
| 7,963,399 B2 | 6/2011 | Böhm et al. |
| 7,997,831 B2 | 8/2011 | Gilbert et al. |
| 8,032,200 B2 | 10/2011 | Tearney et al. |
| 8,080,422 B2 | 12/2011 | Neas et al. |
| 8,123,044 B2 | 2/2012 | Johnson et al. |
| 8,149,402 B2 | 4/2012 | Rich |
| 8,158,122 B2 | 4/2012 | Hampson et al. |
| 8,173,001 B2 | 5/2012 | Quake et al. |
| 8,174,394 B2 | 5/2012 | Ridder et al. |
| 8,198,092 B2 | 6/2012 | Durack et al. |
| 8,206,987 B2 | 6/2012 | Durack et al. |
| 8,209,987 B2 | 7/2012 | Hautman et al. |
| 8,210,209 B2 | 7/2012 | Gilbert et al. |
| 8,277,764 B2 | 10/2012 | Gilbert et al. |
| 8,388,822 B2 | 3/2013 | Quake et al. |
| 8,408,399 B2 | 4/2013 | Böhm et al. |
| 8,502,148 B2 | 8/2013 | Wagner et al. |
| 8,529,161 B2 | 9/2013 | Gilbert et al. |
| 8,563,325 B1 | 10/2013 | Bartsch et al. |
| 8,567,608 B2 | 10/2013 | Deshpande et al. |
| 8,569,069 B2 | 10/2013 | Durack |
| 8,623,295 B2 | 1/2014 | Gilbert et al. |
| 8,727,131 B2 | 5/2014 | Deshpande et al. |
| 8,731,860 B2 | 5/2014 | Charles et al. |
| 8,863,962 B2 | 10/2014 | Johnson et al. |
| 8,941,062 B2 | 1/2015 | Wagner et al. |
| 8,961,904 B2 | 2/2015 | Xia et al. |
| 8,964,184 B2 | 2/2015 | Gilbert et al. |
| 8,981,298 B2 | 3/2015 | Wagner et al. |
| 9,000,357 B2 | 4/2015 | Mueth et al. |
| 9,003,869 B2 | 4/2015 | Wagner et al. |
| 9,011,797 B2 | 4/2015 | Gilbert et al. |
| 9,109,195 B2 | 8/2015 | Zimmermann et al. |
| 9,140,690 B2 | 9/2015 | Mueth et al. |
| 9,255,874 B2 | 2/2016 | Sharpe et al. |
| 9,260,693 B2 | 2/2016 | Johnson et al. |
| 9,335,247 B2 | 5/2016 | Sharpe et al. |
| 9,335,295 B2 | 5/2016 | Mueth et al. |
| 9,339,850 B2 | 5/2016 | Deshpande et al. |
| 9,365,822 B2 | 6/2016 | Seidel et al. |
| 9,377,400 B2 | 6/2016 | Wagner et al. |
| 9,446,912 B2 | 9/2016 | Gilbert et al. |
| 9,485,984 B2 | 11/2016 | Burbank et al. |
| 9,550,215 B2 | 1/2017 | Deshpande et al. |
| 9,588,100 B2 | 3/2017 | Appleyard et al. |
| 9,618,442 B2 | 4/2017 | Sharpe et al. |
| 9,683,922 B2 | 6/2017 | Wagner et al. |
| D791,338 S | 7/2017 | Morkos et al. |
| 9,752,976 B2 | 9/2017 | Gilbert et al. |
| 9,781,918 B2 | 10/2017 | Zimmermann et al. |
| 9,802,767 B2 | 10/2017 | Gilbert et al. |
| 9,823,252 B2 | 11/2017 | Gilbert et al. |
| 9,835,552 B2 | 12/2017 | Wagner |
| D815,754 S | 4/2018 | Morkos et al. |
| 9,943,847 B2 | 4/2018 | Gilbert et al. |
| 9,964,968 B2 | 5/2018 | Sharpe et al. |
| 10,025,322 B2 | 7/2018 | Lofstrom et al. |
| 10,029,283 B2 | 7/2018 | Deshpande et al. |
| 10,175,159 B2 | 1/2019 | Wagner et al. |

(56) References Cited

U.S. PATENT DOCUMENTS

| | | |
|---|---|---|
| 10,180,388 B2 | 1/2019 | Wagner |
| 10,216,144 B2 | 2/2019 | Mueth et al. |
| 10,315,194 B2 | 6/2019 | Akiyama et al. |
| 11,187,224 B2 | 11/2021 | Xia et al. |
| 1,119,387 A1 | 12/2021 | Wagner et al. |
| 11,243,494 B2 | 2/2022 | Mueth et al. |
| 11,331,670 B2 * | 5/2022 | Aguirre ............ B01L 3/502776 |
| 2002/0005354 A1 | 1/2002 | Spence et al. |
| 2002/0027649 A1 | 3/2002 | Chudner |
| 2002/0042042 A1 | 4/2002 | Fahy |
| 2002/0058332 A1 | 5/2002 | Quake et al. |
| 2002/0106716 A1 | 8/2002 | Leboeuf et al. |
| 2002/0115208 A1 | 8/2002 | Mitchell et al. |
| 2002/0176069 A1 | 11/2002 | Hansen et al. |
| 2002/0198928 A1 | 12/2002 | Bukshpan et al. |
| 2003/0007894 A1 | 1/2003 | Wang et al. |
| 2003/0032204 A1 | 2/2003 | Walt et al. |
| 2003/0044832 A1 | 3/2003 | Blankenstein |
| 2003/0054365 A1 | 3/2003 | Xu et al. |
| 2003/0054558 A1 | 3/2003 | Kurabayashi et al. |
| 2003/0068646 A1 | 4/2003 | Singh et al. |
| 2003/0047676 A1 | 6/2003 | Grier et al. |
| 2003/0113709 A1 | 6/2003 | Alivisatos et al. |
| 2003/0175944 A1 | 9/2003 | Yang et al. |
| 2003/0175980 A1 | 9/2003 | Hayenga et al. |
| 2003/0186426 A1 | 10/2003 | Brewer et al. |
| 2004/0043506 A1 | 3/2004 | Haussecker et al. |
| 2004/0079893 A1 | 4/2004 | Dietz et al. |
| 2004/0089798 A1 | 5/2004 | Gruber et al. |
| 2004/0144648 A1 | 7/2004 | Jacobson et al. |
| 2004/0161772 A1 | 8/2004 | Bohm et al. |
| 2004/0166504 A1 | 8/2004 | Rossier et al. |
| 2004/0206399 A1 | 10/2004 | Heller et al. |
| 2004/0217297 A1 | 11/2004 | Moses et al. |
| 2004/0229349 A1 | 11/2004 | Daridon |
| 2004/0266022 A1 | 12/2004 | Sundararajan et al. |
| 2005/0037471 A1 | 2/2005 | Liu et al. |
| 2005/0061962 A1 | 3/2005 | Mueth et al. |
| 2005/0103690 A1 | 5/2005 | Kawano et al. |
| 2005/0112541 A1 | 5/2005 | Durack et al. |
| 2005/0121604 A1 | 6/2005 | Mueth et al. |
| 2005/0123450 A1 | 6/2005 | Gilbert et al. |
| 2005/0124869 A1 | 6/2005 | Hefti et al. |
| 2005/0148085 A1 | 7/2005 | Larsen |
| 2005/0153354 A1 | 7/2005 | Gilmanshin |
| 2005/0190372 A1 | 9/2005 | Dogariu |
| 2005/0196876 A1 | 9/2005 | Chan et al. |
| 2005/0207940 A1 | 9/2005 | Butler et al. |
| 2005/0207943 A1 | 9/2005 | Puzey |
| 2006/0013270 A1 | 1/2006 | Yumoto et al. |
| 2006/0035273 A1 | 2/2006 | Quake et al. |
| 2006/0043301 A1 | 3/2006 | Mantele et al. |
| 2006/0058167 A1 | 3/2006 | Ragusa et al. |
| 2006/0078888 A1 | 4/2006 | Griffiths et al. |
| 2006/0105453 A1 | 5/2006 | Brenan et al. |
| 2006/0152707 A1 | 7/2006 | Kanda |
| 2006/0170912 A1 | 8/2006 | Mueth et al. |
| 2006/0252047 A1 | 11/2006 | Ekstrom et al. |
| 2006/0257089 A1 | 11/2006 | Mueth et al. |
| 2006/0263829 A1 | 11/2006 | Evans et al. |
| 2007/0009386 A1 | 1/2007 | Padmanabhan et al. |
| 2007/0078348 A1 | 4/2007 | Holman |
| 2007/0114172 A1 | 5/2007 | Mueth et al. |
| 2007/0128082 A1 | 6/2007 | Yang et al. |
| 2007/0207551 A1 | 9/2007 | Glensbjerg |
| 2007/0247620 A1 | 10/2007 | Koo |
| 2007/0248958 A1 | 10/2007 | Jovanovich et al. |
| 2007/0255362 A1 | 11/2007 | Levinson |
| 2008/0003685 A1 | 1/2008 | Goix et al. |
| 2008/0014574 A1 | 1/2008 | Viator et al. |
| 2008/0021674 A1 | 1/2008 | Puskas |
| 2008/0069733 A1 | 3/2008 | Maltezo et al. |
| 2008/0144037 A1 | 6/2008 | Mueth et al. |
| 2008/0166188 A1 | 7/2008 | Gilbert et al. |
| 2008/0195020 A1 | 8/2008 | Cabuz et al. |
| 2008/0213821 A1 | 9/2008 | Liu et al. |
| 2008/0248966 A1 | 10/2008 | Hansen et al. |
| 2008/0261295 A1 | 10/2008 | Butler et al. |
| 2008/0292555 A1 | 11/2008 | Ye et al. |
| 2008/0299013 A1 | 12/2008 | Trieu et al. |
| 2008/0309919 A1 | 12/2008 | Birmingham et al. |
| 2008/0311005 A1 | 12/2008 | Kim et al. |
| 2009/0004652 A1 | 1/2009 | Rubin et al. |
| 2009/0029870 A1 | 1/2009 | Ward et al. |
| 2009/0032449 A1 | 2/2009 | Mueth et al. |
| 2009/0042241 A1 | 2/2009 | Yu-Chong et al. |
| 2009/0051912 A1 | 2/2009 | Salazar et al. |
| 2009/0114285 A1 | 5/2009 | Hashimoto et al. |
| 2009/0125242 A1 | 5/2009 | Choi et al. |
| 2009/0141279 A1 | 6/2009 | Hillmer |
| 2009/0156932 A1 | 6/2009 | Zharov |
| 2009/0170149 A1 | 7/2009 | Viator et al. |
| 2009/0176271 A1 | 7/2009 | Durack et al. |
| 2009/0201504 A1 | 8/2009 | Ho et al. |
| 2009/0225319 A1 | 9/2009 | Lee et al. |
| 2009/0281250 A1 | 11/2009 | DeSimone et al. |
| 2009/0290156 A1 | 11/2009 | Popescu et al. |
| 2010/0044570 A1 | 2/2010 | McGill et al. |
| 2010/0068723 A1 | 3/2010 | Jovanovich et al. |
| 2010/0079516 A1 | 4/2010 | Nakazawa |
| 2010/0167336 A1 | 7/2010 | Son et al. |
| 2010/0171954 A1 | 7/2010 | Quake et al. |
| 2010/0216208 A1 | 8/2010 | Mueth et al. |
| 2010/0248362 A1 | 9/2010 | Durack et al. |
| 2010/0330693 A1 | 12/2010 | Chapin et al. |
| 2011/0001963 A1 | 1/2011 | Durack |
| 2011/0003303 A1 | 1/2011 | Pagano et al. |
| 2011/0003324 A1 | 1/2011 | Durack |
| 2011/0003325 A1 | 1/2011 | Durack |
| 2011/0003330 A1 | 1/2011 | Durack |
| 2011/0008764 A1 | 1/2011 | Silva et al. |
| 2011/0008767 A1 | 1/2011 | Durack |
| 2011/0008817 A1 | 1/2011 | Durack |
| 2011/0008818 A1 | 1/2011 | Durack |
| 2011/0075928 A1 | 3/2011 | Jeong et al. |
| 2011/0076712 A1 | 3/2011 | Gilligan et al. |
| 2011/0090500 A1 | 4/2011 | Hu et al. |
| 2011/0096327 A1 | 4/2011 | Papautsky et al. |
| 2011/0190146 A1 | 8/2011 | Boehm et al. |
| 2011/0223654 A1 | 9/2011 | Holman et al. |
| 2011/0256523 A1 | 10/2011 | Mendele et al. |
| 2011/0263747 A1 | 10/2011 | Doyle et al. |
| 2011/0294139 A1 | 12/2011 | Takeda |
| 2012/0009619 A1 | 1/2012 | Gilbert et al. |
| 2012/0028366 A1 | 2/2012 | Krager et al. |
| 2012/0033220 A1 | 2/2012 | Kotidis et al. |
| 2012/0033697 A1 | 2/2012 | Goyal et al. |
| 2012/0081709 A1 | 4/2012 | Durack |
| 2012/0082362 A1 | 4/2012 | Diem et al. |
| 2012/0107805 A1 | 5/2012 | Neas et al. |
| 2012/0122084 A1 | 5/2012 | Wagner et al. |
| 2012/0138152 A1 | 6/2012 | Villarruel et al. |
| 2012/0183947 A1 | 7/2012 | Mueth et al. |
| 2012/0196356 A1 | 8/2012 | Wagner et al. |
| 2012/0199741 A1 | 8/2012 | Wagner et al. |
| 2012/0199742 A1 | 8/2012 | Wagner et al. |
| 2012/0202237 A1 | 8/2012 | Sedoglavich et al. |
| 2012/0202277 A1 | 8/2012 | Wagner et al. |
| 2012/0202278 A1 | 8/2012 | Wagner et al. |
| 2012/0204628 A1 | 8/2012 | Wagner et al. |
| 2012/0225474 A1 | 9/2012 | Wagner et al. |
| 2012/0225475 A1 | 9/2012 | Wagner et al. |
| 2012/0273054 A1 | 11/2012 | Lou et al. |
| 2012/0287419 A1 | 11/2012 | Sharpe et al. |
| 2012/0295263 A1 | 11/2012 | Cantor et al. |
| 2012/0307244 A1 | 12/2012 | Sharpe et al. |
| 2013/0121877 A1 | 5/2013 | Ono |
| 2013/0164731 A1 | 6/2013 | Cimino et al. |
| 2013/0164773 A1 | 6/2013 | Bardell et al. |
| 2013/0200277 A1 | 8/2013 | Li et al. |
| 2013/0224843 A1 | 8/2013 | Evans et al. |
| 2013/0252237 A1 | 9/2013 | Wagner |
| 2013/0295602 A1 | 11/2013 | Fowler et al. |
| 2013/0313170 A1 | 11/2013 | Bohm et al. |

(56) References Cited

U.S. PATENT DOCUMENTS

| | | |
|---|---|---|
| 2014/0033808 A1 | 2/2014 | Ding et al. |
| 2014/0050540 A1 | 2/2014 | Gilbert et al. |
| 2014/0091014 A1 | 4/2014 | Wagner et al. |
| 2014/0127688 A1 | 5/2014 | Umbarger et al. |
| 2014/0224710 A1 | 8/2014 | Di Carlo et al. |
| 2014/0273192 A1 | 9/2014 | Sharpe et al. |
| 2014/0287243 A1 | 9/2014 | Weber et al. |
| 2014/0318645 A1 | 10/2014 | Koksal et al. |
| 2014/0339446 A1 | 11/2014 | Yamamoto et al. |
| 2014/0361148 A1 | 12/2014 | Popescu et al. |
| 2015/0064694 A1 | 3/2015 | Sadri |
| 2015/0114093 A1 | 4/2015 | Appleyard et al. |
| 2015/0192511 A1 | 7/2015 | Wagner et al. |
| 2015/0198517 A1 | 7/2015 | Simpson et al. |
| 2015/0276588 A1 | 10/2015 | Marshall et al. |
| 2016/0004060 A1 | 1/2016 | Simpson et al. |
| 2016/0123858 A1 | 5/2016 | Kapur et al. |
| 2016/0199835 A1 | 7/2016 | Tachibana et al. |
| 2016/0303563 A1 | 10/2016 | Granier et al. |
| 2016/0368003 A1 | 12/2016 | Vester et al. |
| 2017/0016813 A1 | 1/2017 | Wagner |
| 2017/0181425 A1 | 6/2017 | Burbank et al. |
| 2017/0307505 A1 | 10/2017 | Vrane et al. |
| 2017/0333902 A1 | 11/2017 | Masaeli et al. |
| 2018/0266937 A1 | 9/2018 | de Wagenaar et al. |
| 2019/0025212 A1 | 1/2019 | Evans |
| 2019/0040356 A1 | 2/2019 | Durack et al. |
| 2019/0071725 A1 | 3/2019 | Roti-Roti et al. |
| 2019/0160439 A1 | 5/2019 | Muto et al. |
| 2019/0187044 A1 | 6/2019 | Appleyard et al. |
| 2019/0382720 A1 | 12/2019 | Savage et al. |
| 2019/0390164 A1 | 12/2019 | Morjal et al. |
| 2020/0070152 A1 | 3/2020 | Kasai et al. |
| 2022/0025443 A1 | 1/2022 | Korani et al. |
| 2022/0026341 A1 | 1/2022 | Appleyard et al. |

FOREIGN PATENT DOCUMENTS

| | | |
|---|---|---|
| CN | 1482369 A | 3/2004 |
| CN | 1886315 | 12/2006 |
| CN | 101189504 A | 5/2008 |
| CN | 104862273 A | 8/2015 |
| CN | 1910441 A | 2/2017 |
| CN | 105940301 A | 6/2017 |
| CN | 101201313 A | 6/2018 |
| CN | 109022562 A | 12/2018 |
| CN | 109221081 A | 1/2019 |
| CN | 109497040 A | 3/2019 |
| CN | 109517787 A | 3/2019 |
| EP | 0057907 | 8/1982 |
| EP | 0282994 | 9/1988 |
| EP | 0679325 | 11/1995 |
| EP | 0471758 B1 | 9/1996 |
| FR | 2798557 | 3/2001 |
| GB | 502971 A | 3/1939 |
| GB | 2507959 A | 5/2014 |
| JP | 57131451 | 8/1982 |
| JP | 58090513 | 5/1983 |
| JP | S6426125 A | 1/1989 |
| JP | 64074451 | 3/1989 |
| JP | H02105041 A | 4/1990 |
| JP | 03297385 | 12/1991 |
| JP | H0526799 | 2/1993 |
| JP | 06265452 | 9/1994 |
| JP | 06327494 | 11/1994 |
| JP | 07024309 | 1/1995 |
| JP | H07286953 A | 10/1995 |
| JP | 2552582 | 11/1996 |
| JP | H10512952 A | 12/1998 |
| JP | H11508182 | 7/1999 |
| JP | 2000146819 A | 5/2000 |
| JP | 2000512541 | 9/2000 |
| JP | 2001504936 | 4/2001 |
| JP | 2002503334 | 1/2002 |
| JP | 2002153260 | 5/2002 |
| JP | 2003106980 A | 4/2003 |
| JP | 2003515738 A | 5/2003 |
| JP | 2004093553 A | 3/2004 |
| JP | 2005502482 | 1/2005 |
| JP | 2005530986 A | 10/2005 |
| JP | 2006524054 A | 10/2006 |
| JP | 2007148981 | 6/2007 |
| JP | 2007514522 A | 6/2007 |
| JP | 2007515936 A | 6/2007 |
| JP | 2008533440 A | 8/2008 |
| JP | 2008261295 A | 10/2008 |
| JP | 2009085872 A | 4/2009 |
| JP | 2009115672 A | 5/2009 |
| JP | 2009162660 A | 7/2009 |
| JP | 2010117197 A | 5/2010 |
| JP | 2010151777 A | 7/2010 |
| JP | 2010190680 A | 9/2010 |
| JP | 2011145185 | 7/2011 |
| JP | 2014503195 A | 2/2014 |
| WO | WO9622521 A1 | 7/1996 |
| WO | WO9700442 | 1/1997 |
| WO | WO1997030338 A1 | 8/1997 |
| WO | WO9739338 | 10/1997 |
| WO | WO9747390 | 12/1997 |
| WO | WO9810267 | 3/1998 |
| WO | WO99/39223 | 8/1999 |
| WO | WO0070080 A1 | 11/2000 |
| WO | WO0118400 | 3/2001 |
| WO | WO0131315 | 5/2001 |
| WO | WO2001040766 A1 | 6/2001 |
| WO | WO0185913 A2 | 11/2001 |
| WO | WO2002006778 A1 | 1/2002 |
| WO | WO0241906 A2 | 5/2002 |
| WO | WO02081183 A1 | 10/2002 |
| WO | WO02087792 | 11/2002 |
| WO | WO03024163 | 3/2003 |
| WO | WO03062867 | 7/2003 |
| WO | WO03078065 | 9/2003 |
| WO | WO2004012133 A2 | 2/2004 |
| WO | WO2004029221 | 4/2004 |
| WO | WO2004043506 A1 | 5/2004 |
| WO | WO2004088283 A3 | 10/2004 |
| WO | WO2005023391 A3 | 3/2005 |
| WO | WO2005037471 A1 | 4/2005 |
| WO | WO2005075629 A1 | 8/2005 |
| WO | WO2006119806 A1 | 11/2006 |
| WO | WO2007008495 A2 | 1/2007 |
| WO | WO2007133710 A2 | 11/2007 |
| WO | WO2008114458 A1 | 9/2008 |
| WO | WO2008126064 A2 | 10/2008 |
| WO | WO2008130977 A2 | 10/2008 |
| WO | WO2009032449 A1 | 3/2009 |
| WO | WO2009134395 A2 | 11/2009 |
| WO | WO2010129441 | 11/2010 |
| WO | WO2012068287 A3 | 5/2012 |
| WO | WO2012112641 A1 | 8/2012 |
| WO | WO2013018273 A1 | 2/2013 |
| WO | WO2013173446 A1 | 11/2013 |
| WO | 2015038494 | 3/2015 |
| WO | WO2015063552 A2 | 5/2015 |
| WO | WO2018047011 A2 | 3/2018 |
| WO | WO2018151680 A1 | 8/2018 |
| WO | 2019236569 A1 | 12/2019 |
| WO | WO2020092321 A1 | 5/2020 |
| WO | WO2020182193 A1 | 9/2020 |

OTHER PUBLICATIONS

Shapiro et al., "Pratical Flow Cytometry," Fourth Edition, New Jersey: John W. Wiley & Sons, 2003, 52 pages.

Sharpe et al., "Advances in Flow Cytometry for Sperm Sexing," Theriogenology, vol. 71, 2009, pp. 4-10.

Short, "Raman Spectroscopy Detects Biochemical Changes Due to Proliferation in Mammalian Cell Cultures," Biophysical Journal, vol. 88, Jun. 2005, pp. 4274-4288.

USPTO, "Non-Final Office Action," issued in connection with U.S. Appl. No. 15/226,899, mailed Apr. 12, 2018, 14 pages.

(56) References Cited

OTHER PUBLICATIONS

USPTO, "Notice of Allowance," issued in connection with U.S. Appl. No. 15/226,899, mailed Aug. 23, 2018, 5 pages.
USPTO, "Notice of Allowance," issued in connection with U.S. Appl. No. 15/226,899, mailed Sep. 20, 2018, 6 pages.
USPTO, "Final Office Action," issued in connection with U.S. Appl. No. 15/174,681, mailed Jan. 2, 2018, 15 pages.
USPTO, "Final Office Action," issued in connection with U.S. Appl. No. 15/174,681, mailed Sep. 14, 2018, 17 pages.
USPTO, "Non-Final Office Action," issued in connection with U.S. Appl. No. 15/174,681, mailed May 4, 2017, 13 pages.
USPTO, "Non-Final Office Action," issued in connection with U.S. Appl. No. 15/174,681, mailed Apr. 5, 2018, 16 pages.
USPTO, "Notice of Allowance," issued in connection with U.S. Appl. No. 15/174,681, mailed Nov. 27, 2018, 10 pages.
USPTO, "Final Office Action," issued in connection with U.S. Appl. No. 13/298,148, mailed Oct. 18, 2013, 46 pages.
USPTO, "Non-Final Office Action," issued in connection with U.S. Appl. No. 13/298,148, mailed Feb. 5, 2013, 66 pages.
USPTO, "Notice of Allowance," issued in connection with U.S. Appl. No. 13/298,148, mailed Sep. 19, 2014, 9 pages.
USPTO, "Office Action," issued in connection with U.S. Appl. No. 13/298,148, mailed Sep. 28, 2012, 5 pages.
USPTO, "Final Office Action," issued in connection with U.S. Appl. No. 13/894,831, mailed Sep. 10, 2015, 11 pages.
USPTO, "Final Office Action," issued in connection with U.S. Appl. No. 13/894,831, mailed Jun. 15, 2017, 19 pages.
USPTO, "Non-Final Office Action," issued in connection with U.S. Appl. No. 13/894,831, mailed Dec. 23, 2014, 11 pages.
USPTO, "Non-Final Office Action," issued in connection with U.S. Appl. No. 13/894,831, mailed Oct. 5, 2016, 17 pages.
USPTO, "Notice of Allowance," issued in connection with U.S. Appl. No. 13/894,831, mailed Apr. 1, 2016, 8 pages.
USPTO, "Notice of Allowance," issued in connection with U.S. Appl. No. 13/894,831, mailed Sep. 5, 2017, 9 pages.
Wang et al., Detection of endogenous biomolecules in Barrett's esophagus by Fourier transform infrared spectroscopy, PNAS, vol. 104, No. 40, Oct. 2, 2007, p. 15864-15869.
Webster, Merriam, "Definition of "successive," Merriam Webster's Online Dictionary, accessed at http://www.merriamwebster.com/dictionary/successive," Jul. 3, 2013, 1 page.
Weida et al., "Quantum cascade laser-based replacement for FTIR microscopy", Proc. SPIE 7902, Imaging, Manipulation, and Analysis of Biomolecules, Cells, and Tissues IX, 79021C, Feb. 11, 2011; 7 pages; https://doi.org/10.1117/12.873954.
International Bureau, "International Preliminary Report on Patentability," issued in connection with International Patent Application No. PCT/IB2017/001289, mailed Mar. 21, 2019, 12 pages.
International Search Report and Written Opinion for Application Serial No. PCT/IB2017/001289, dated Apr. 3, 2018, 21 pages.
Mehrnoush Malek et al: flowDensity: reproducing manual gating of flow cytometry data by automated density-based cell population identification, Bioinformatics., vol. 31, No. 4, Oct. 16, 2014 (Oct. 16, 2014), pp. 606-607.
International Search Report and Written Opinion for Application Serial No. PCT/IB2018/001641, dated Nov. 5, 2019, 4 pages.
China Patent Office, "The Fourth Office Action," issued in connection with China Patent Application No. 201480071952.0, Feb. 3, 2021, 25 pages.
Japan Patent Office, "Notice of Reasons for Refusal," issued in connection with Japan Patent Application No. 2019-088655, Oct. 9, 2020, 5 pages.
Johnson LA et al., Flow sorting of X and Y chromosome-bearing spermatozoa into two populations, Gamete Research. Jan. 1987. 16(1):1-9. (Johnson 1987).
Paape et al., Flow Cytometry: A Versatile Tool for Studies on Cells From Domestic Animals, National Cytometry Symposium, Abstract Only, Dec. 14, 1997, https://www.ars.usda.gov/research/publications/publication/?seqNo115=86408.
Keij, J.F. et al., "High-Speed Photodamage Cell Selection Using a Frequency-Doubled Argon Ion Laser." Cytometry 19(1995): 209-216. (Keij 1995).
Keij, J.F., "Introduction to High-Speed Flow Sorting." Flow and Image Cytometry. Series H: Cell Biology, 95 (1996): 213-227. (Keij 1996).
Johnson et al. "The Beltsville sperm sexing technology: high-speed sperm sorting gives improved sperm output for in vitro fertilization and AI." J Anim Sci 1999. 77:213-220.
Counterclaim Defendants Abs Global Inc.'s and Genus PLC's Invalidity Contentions. *Abs Global, Inc.*, v. *Inguran, LLC D/B/A Sexing Technologies and. Xy, LLC* v. *Genus PLC*. Case No. 14-cv-503 United States District Court for the Western District of Wisconsin; Decided Aug. 14, 2019, pp. 1, 43-114, and 168-177.
ABS Global, Inc. And Genus PLC's Renewed Motion For Judgment As A Matter Of Law That The Asserted Claims Of The '987 Patent Are Invalid For Lack Of Enablement And, In The Alternative, For A New Trial. *ABS Global, Inc.* v. *Inguran, LLC & Xy, LLC* v. *Genus PLC*. Case: 3:14-cv-00503-wmc. Filed on Jul. 3, 2020, 40 pages.
Brief in Support of ABS Global, Inc. And Genus PLC's Motion for Judgment as A Matter of Law That the Asserted Claims Of The '987 Patent Are Not Enabled. *Inguran, LLC d/b/a STGenetics, Xy, LLC, and Cytonome/ST, LLC*, Plaintiffs/Counterclaim-Defendants, v.*ABS Global, Inc., Genus PLC, and Premium Genetics (UK) Ltd*, Defendants/Counterclaim-Plaintiffs. Case: 3:17-cv-00446-wmc. Filed Sep. 6, 2019.
ABS Global, Inc. And Genus Plc Renewed Motion for Judgment As A Matter Of Law That The Asserted Claims Of The 987 Patent Are Invalid For Lack Of Enablement And, In The Alternative, For A New Trial. *Inguran, LLC d/b/a STGenetics, Xy, LLC, and Cytonome/ST, LLC*, Plaintiffs/Counterclaim-Defendants, v.*ABS Global, Inc., Benus PLC, and Premium Genetics (UK) Ltd*, Defendants/Counterclaim-Plaintiffs. Case: 3:17-cv-00446-wmc. filed Jul. 3, 2020, 72 pages.
ABS Global, Inc. And Genus PLC's Reply In Support Of Their Renewed Motion For Judgment As A Matter Of Law That The Asserted Claims Of The '987 Patent Are Invalid For Lack Of Enablement And, In The Alternative, For A New Trial. *Inguran, LLC d/b/a STGenetics, Xy, LLC, and Cytonome/ST, LLC*, Plaintiffs/Counterclaim-Defendants, v. *Abs Global, Inc., Genus PLC, and Premium Genetics (UK) Ltd*, Defendants/Counterclaim-Plaintiffs. Case: :17-cv-00446-wmc. Filed Aug. 17, 2020, 40 pages.
ABS Global, Inc. and Genus PLC's Motion For Judgment As A Matter Of Law That The Asserted Claims Of The 987 And '092 Patents Are Invalid. *ABS Global, Inc.*, Plaintiff/Counterclaim Defendant, v. *Inguran, LLC d/b/a Sexing Technologies*, Defendant/Counterclaim Plaintiff, and *Xy, LLC*, Intervenor-Defendant/Counterclaim Plaintiff, v. *Genus PLC*, Counterclaim Defendant. Case: 3:14-cv-00503-wmc. Filed Aug. 9, 2016, 35 pages.
ABS Global, Inc. and Genus PLC's Rule 50(8) Motion For Judgment As A Matter Of Law And Rule 59 Motion For A New Trial. *ABS Global, Inc.*, Plaintiff/Counterclaim Defendant, v. *Inguran, LLC d/b/a Sexing Technologies*, Defendant/Counterclaim Plaintiff, and *Xy, LLC*, Intervenor-Defendant/Counterclaim Plaintiff, v. *Genus PLC*, Counterclaim Defendant. Case: 3:14-cv-00503-wmc. Filed Sep. 2, 2016, 61 pages.
Opinion and Order of the United States District Court For The Western District Of Wisconsin. Plaintiff/Counterclaim Defendant, v. *Inguran, LLC d/b/a Sexing Technologies*, Defendant/Counterclaim Plaintiff, and *Xy, LLC*, Intervenor-Defendant/Counterclaim Plaintiff, v. *Genus PLC*, Counterclaim Defendant. Case: 3:14-cv-00503-wmc. riled Mar. 31, 2017, 18 pages.
Appeal from the United States District Court for the Western District of Wisconsin. No. 14-CV-503. *ABS Global, NC.*, Plaintiff/Counterclaim Defendant-Appellant, and *Genus PLC*, Counterclaim Defendant-Appellant, v. *Inguran, LLC, doing business as Sexing Technologies*, Defendant/Counterclaim Plaintiff-Appellee, and *Xy, LLC*, Intervening Defendant/Counterclaim Plaintiff-Appellee. Case: 3:14-cv-00503-wmc. Filed: May 12, 2011, 200 pages.
Judge's Opinion & Order in Case No. 14-cv-503-wmc. Plaintiff/Counterclaim Defendant, v. *Inguran, LLC dib/a Sexing Technologies*, Defendant/Counterclaim Plaintiff, and *Xy, LLC*, Intervenor-

(56) References Cited

OTHER PUBLICATIONS

Defendant/Counterclaim Plaintiff, v. *Genus PLC*, Counterclaim Defendant. Case: 3:14-cv-00503-wmc. Filed Jul. 21, 2016, 41 pages.
ABS Global Inc. and Genus PLC's Reply in Support of Their Motion for Claim Construction and Partial Summary Judgment, *ABS Global, Inc. v. Inguran, LLC d/b/a Sexing Technologies*, Case No. 14-cv-503, United States District Court for the Western District of Wisconsin. Mar. 7, 2016, 55 pages.
USPTO, "Final Office Action," issued in connection with U.S. Appl. No. 16/741,608, dated Oct. 19, 2022, 12 pages.
USPTO, "Non-Final Office Action," issued in connection with U.S. Appl. No. 17/851,319, dated Nov. 2, 2022, 12 pages.
USPTO, "Final Office Action," issued in connection with U.S. Appl. No. 16/279,430, dated Dec. 6, 2022, 18 pages.
New Zealand IP Office, "First Examination Report," issued in connection with New Zealand Patent Application No. 751869, mailed Aug. 12, 2022, 3 pages.
Canadian Office Action, Application No. 3,034,007, mailed Aug. 25, 2022, 3 pages.
Altendorf et al., "Results Obtained Using a Prototype Microfluidics-Based Hematology Analyzer," in Proceedings of the micro TAS 1998 Symposium, 73-76 (Oct. 1998).
Nieuwenhuis et al., "Particle-Shape Sensing-Elements for Integrated Flow Cytometer," in Proceedings of the microTAS 2001 Symposium, 357-358 (Oct. 21, 2001).
Nieuwenhuis et al. "Virtual Flow Channel: A Novel Micro-fluidics System with Orthogonal, Dynamic Control of Sample Flow Dimensions," in Proceedings of the microTAS 2002 Symposium, vol. 1, 103-105 (Nov. 3, 2002).
Nieuwenhuis, J., et al. "Integrated flow-cells for novel adjustable sheath flows." Lab Chip, 2003, 3, 56-61 (Mar. 2003).
Shoji, S., et al. "Design and fabrication of micromachined chemical/biochemical systems." Riken Rev., vol. 36, pp. 8-11, 2001.
Lin, C., et al. "A Novel Microflow Cytometer with 3-dimensional Focusing Utilizing Dielectrophoretic and Hydrodynamic Forces." The Sixteenth Annual International Conference on Micro Electro Mechanical Systems, 2003. MEMS-03 Kyoto. IEEE, Kyoto, Japan, 2003, pp. 439-442.
Miyake et al., "A Development of Micro Sheath Flow Chamber," in Proceedings of the IEEE Micro Electro Mechanical Systems Workshop 1991, 265-270 (Jan. 1991).
Tashiro et al., "Design and Simulation of Particles and Biomolecules Handling Micro Flow Cells with Three-Dimensional Sheath Flow," in Proceedings of the microTAS 2000 Symposium, 209-212 (May 14, 2000).
Weigl, B. et al. "Design and Rapid Prototyping of Thin-Film Laminate-Based Microfluidic Devices." Biomedical Microdevices, 3:4, pp. 267-274, 2001.
Blankenstein, G. et al. "Modular concept of a laboratory on a chip for chemical and biochemical analysis." Biosensors & Bioelectronics, vol. 13. No 3-4, pp. 427-438, 1998.
Shapiro, Practical Flow Cytometry, 15-17, 133-135 (3rd ed. 1995).
Shapiro, Practical Flow Cytometry, 55-57, 166-169 (4th ed. 2003).
International Search Report for PCT Patent Application No. PCT/IB2014/001425 dated Apr. 28, 2015.
Herweijer, H. et al., "High Speed Photodamage Cell Selection Using Bromodeoxyuridine/Hoechst 33342 Photosensitized Cell Killing", Radiobiological Institute TNO, Rotterdam, The Netherlands, Jun. 1, 1987.
Johnson, L.A., et al., "Sex Preselection: High-Speed Flow Cytometric Sorting of X and Y Sperm for Maximum Efficiency" U.S. Dept. of Agriculture, Beltsville, MD, Sep. 23, 1999.
Bazyer H., et al., "Views and Reviews—Compact 151W Green Laser with U-Type Resonator for Prostate Surgery", Optics & Laser Technology, vol. 47, Apr. 27, 2013, 237-241.
Keij, J. et al., "High-Speed Photodamage Cell Sorting: An Evaluation of the Zapper Prototype", Methods in Cell Biology, 1994; pp. 371-386, vol. 42, Chapter 22, Academic Press, Inc.

International Search Report and Written Opinion issued on Mar. 7, 2014 in connection with PCT/US2013/050669.
Kachel, V, et al., "Uniform Lateral Orientation, caused by Flow Forces, of Flat Particles in Flow-Through Systems", The Journal of Histochemistry and Cytochemistry, vol. 25, No. 7, pp. 774-780, 1977.
Notice of Allowance issued in U.S. Appl. No. 13/943,322 on Sep. 12, 2014.
Fulwler, M., "Hydrodynamic Orientation of Cells", The Journal of Histochemistry and Cytochemistry, vol. 25, No. 7, pp. 781-783, 1977.
Khodjakov A., et al., "A Synergy of Technologies: Combining Laser Microsurgery with Green Fluorescent Protein Tagging", Cell Motility and the Cytoskeleton 38:311-317 (1997), Division of Molecular Medicine and Department of Biomedical Sciences, Albany, New York.
Canadian Office Action, Application No. 2,929,275, mailed May 4, 2020, 8 pages.
Australian Office Action, Application No. 2019202882, mailed Mar. 26, 2020, 3 pages.
Brazilian Office Action, Application No. BR122017012966-0, mailed Jun. 2, 2020, 6 pages.
Japan Patent Office, "Reconsideration Report before Appeal," issued in connection with Japanese Patent Application No. 2016-551082, mailed Jul. 12, 2019, 17 pages.
Intellectual Property India, "Examination Report," issued in connection with Indian Patent Application No. 3425/DELNP/2015, mailed Jan. 20, 2020, 6 pages.
European Patent Office, "Extended European Search Report," issued in connection with patent application No. 19182993.6, mailed Oct. 21, 2019, 11 pages.
China National Intellectual Property Administration, "Second Office Action," issued in connection with Chinese Patent Application No. 201480071952.0, mailed Nov. 26, 2018, 34 pages.
China National Intellectual Property Administration, "Decision of Rejection," issued in connection with Chinese Patent Application No. 201480071952.0, mailed Mar. 4, 2019, 19 pages.
IP Australia, "Examination Report No. 1 for Standard Patent Application," issued in connection with Australian Patent Application No. 2014343391, mailed Sep. 4, 2018, 3 pages.
International Preliminary Report on Patentability, issued in connection with application PCT/IB2014/001425, May 3, 2016, 11 pages.
Japan Patent Office, "Non Final Notice of Reasons for Rejection," issued in connection with Japanese Patent Application No. 2016-551082, mailed Apr. 24, 2018, 5 pages.
New Zealand IP Office, "First Examination Report," issued in connection with New Zealand Patent Application No. 720575, mailed Sep. 9, 2016, 5 pages.
New Zealand IP Office, "Further Examination Report," issued in connection with New Zealand Patent Application No. 720575, mailed Apr. 28, 2017, 3 pages.
State Intellectual Property Office of People's Republic of China, "Notification of First Office Action," issued in connection with Chinese Patent Application No. 201480071952.0, mailed Mar. 16, 2018, 31 pages.
New Zealand IP Office, "Further Examination Report," issued in connection with New Zealand Patent Application No. 735496, mailed Aug. 31, 2018, 2 pages.
Drobnis et al., Cold Shock Damage is due to Lipid Phase Transitions in Cell Membranes: A Demonstration Using Sperm as a Model, The Journal of Experimental Zoology, 1993, 265:432-437.
Way et al., Comparison of four staining methods for evaluating acrosome status and viability of ejaculated and cauda epididymal bull spermatozoa, Theriogenology, 1995, 43(8): 1301-1316.
Marian et al., Hypo-osmotic Shock Induces an Osmolality-dependent Permeabilization and Structural Changes in the Membrane of Carp Sperm, 1993, 41(2):291-297.
Molecular Probes Inc., Product Information, Influx Pinocytic Cell-Loading Reagent (1-14402), Revised Feb. 1, 2001, 1-7.
Parks, Processing and Handling Bull Semen for Artificial Insemination—Don't Add Insult to Injury!, Department of Animal Sciences, Cornell University, 2013, retrieved on May 29, 2015, retrieved from the internet: http://www/ansci.cornell.edu/bullsemen.pdf.

(56) References Cited

OTHER PUBLICATIONS

Mammal (Online Datasheet), Wikipedia, 2003, retrieved on Aug. 13, 2018, retrieved from internet: http://web.archive.org/web/20031230110838/hllps://en.wikipedia.org/wiki/Mammal.
International Searching Authority, "International Search Report and Written Opinion," issued in connection with International Patent Application No. PCT/IB2016/000295, mailed Oct. 14, 2016, 19 pages.
International Bureau, "International Preliminary Report on Patentability," issued in connection with International Patent Application No. PCT/IB2016/000295, mailed Aug. 31, 2017, 14 pages.
Japan Patent Office, "Office Action," issued in connection with Japanese Patent Application No. 2017-543990, Jul. 31, 2019, 23 pages.
Di Carlo et al. "Equilibrium Separation and Filtration of Particles Using Differential Inertial Focusing" BioMEMS Resource Center, Center for Engineering in Medicine and Surgical Services, Massachusetts General Hospital, Anal Chem 2008, 8, 2204-2211.
"Hydraulic Diameter", Neutrium, Apr. 1, 2012, https://neutrium.net/fluid-flow/hydraulic-diameter/ (Year: 2012).
Gossett et al. "Particle Focusing Mechanisms in Curving Confined Flows" Anal. Chem. 2009, 81, 8459-8465 (Year: 2009).
Di Carlo et al. "Continuous inertial focusing, ordering, and separation of particles in microchannels" BioMEMS Resource Center, Center for Engineering in Medicine and Surgical Services, Massachusetts General Hospital, Nov. 27, 2007, PNAS, 18892-18897, vol. 104, No. 48.
Notice of Allowance issued in U.S. Appl. No. 17/525,125 on Jun. 28, 2024.
China National Intellectual Property Administration, "First Examination Report," issued in connection with Chinese Patent Application No. 202080091173.2, mailed Jun. 27, 2024, 11 pages.
USPTO, "Non-Final Office Action," issued in connection with U.S. Appl. No. 17/507,662, mailed Sep. 5, 2024, 28 pages.
New Zealand IP Office, "First Examination Report," issued in connection with New Zealand Patent Application No. 789767, mailed Aug. 29, 2024, 3 pages.
USPTO, "Non-Final Office Action," issued in connection with U.S. Appl. No. 17/496,614, dated Dec. 21, 2022, 9 pages.
UPSTO, "Non-Final Office Action," issued in connection with U.S. Appl. No. 16/852,303, dated Jan. 9, 2023, 30 pages.
European Patent Office, "European Search Report," issued in connection with European Patent Application No. 20792020.8, mailed Dec. 23, 2022, 10 pages.
Brazilian Office Action, Application No. BR112020023607-1, mailed Dec. 12, 2022, 5 pages.
Ron Bardell et al. "Microfluidic disposables for cellular and chemical detection: CFD model results and fluidic verification experiments," Proc. SPIE 4265, Biomedical Instrumentation Based on Micro- and Nanotechnology, May 21, 2001; doi: 10.1117/12.427961 Invited Paper: BiOS 2001 The International Symposium on Biomedical Optics, 2001, San Jose, CA, United States, 14 pages.
Trial Transcript, Sep. 5, 2019 (a.m.); *ABS Global, Inc.* v. *Inguran, LLC d/b/a Sexing Technologies*, Case Nos. 17-cv-446 and 14-cv-503, United States District Court for the Western District of Wisconsin, 14 pages.
Brief in Support of ABS Global, Inc. and Genus PLC's Rule 50(8) Motion for Judgment as a Matter of Law and Rule 59 Motion for a New Trial, *ABS Global, Inc.* v. *Inguran, LLC d/b/a Sexing Technologies*, Case No. 14-cv-503, United States District Court for the Western District of Wisconsin. Filed Sep. 2, 2016. 72 pages.
Inguran, LLC and Xy, LLC's Response To ABS Global, Inc. and Genus PLC's Rule 50(8) Motion Fof Judgment as a Matter of Law and Rule 59 Motion for New Trial, pp. 9-28, 33-36, 73-74. Filed Sep. 23, 2016.
ST's Response To ABS's Renewed Motion for Judgment as a Matter of Law That the Asserted Claims of the '987 Patent Are Invalid for Lack of Enablement and, in the Alternative, for a New Trial, *ABS Global, Inc.* v. *Inguran, LLC d/b/a Sexing Technologies*, Case No. 14-cv-503, United States District Court for the Western District of Wisconsin. Filed: Jul. 24, 2020. 40 pages.
Clinical Laboratory Instruments and In Vitro Diagnostic Reagents, Personnel Department of the State Food and Drug Administration, et al., pp. 17-21, China Medical Science and Technology Publishing House, Oct. 31, 2010.
China Patent Office, "The Fifth Office Action," issued in connection with China Patent Application No. 2014800719520, Oct. 20, 2021, 7 pages.
USPTO, "Non-Final Office Action," issued in connection with U.S. Appl. No. 17/458,947, dated Dec. 15, 2021, 9 pages.
DiCarlo "Inertial Microfluidics: High-Throughput Focusing and Separation of Cells and Particles" BioMEMS Resource Center, Center for Engineering in Medicine, Massachusetts General Hospital, Twelfth International Conference on Miniaturized Systems for Chemistry and Life Sciences, Oct. 12-16, 2008, San Diego, California, USA. 3 pages.
Miyake, Ryo, et al. "Investigation of sheath flow chambers for flow cytometers: Micro machined flow chamber with low pressure loss." JSME International Journal Series B Fluids and Thermal Engineering 40.1 (1997): 106-113.
*Inguran, LLC* v. *ABS Glob., Inc.*, W.D. Wis., Case: 17-cv-446-wmc, Filed Apr. 29, 2019, 61 pages.
Miyake, Ryo, et al. "Flow cytometric analysis by using micromachined flow chamber." JSME International Journal Series B Fluids and Thermal Engineering 43.2 (2000): 219-224.
Shapiro et al., "Practical Flow Cytometry," Fourth Edition, New Jersey: John Wiley & Sons, 2003, 5 pages.
Johnson et al. "Sex preselection in rabbits: live births from X and Y sperm separated by DNA and cell sorting." Biology of Reproduction 41.2 (1989): 199-203.
USPTO, "Notice of Allowance," issued in connection with U.S. Appl. No. 16/864,514, mailed Jan. 3, 2022, 24 pages.
USPTO, "Notice of Allowance," issued in connection with U.S. Appl. No. 16/419,756, mailed Jan. 12, 2022, 16 pages.
USPTO, "Non-Final Office Action," issued in connection with U.S. Appl. No. 16/852,303, dated Jan. 6, 2022, 27 pages.
Intellectual Property India, "Examination Report," issued in connection with Indian Patent Application No. 202147003036, mailed Jan. 4, 2022, 5 pages.
Di Carlo, "Inertial microfluidics." Lab on a Chip 9.21 (2009): 3038-3046.
Intellectual Property India, "Examination Report," issued in connection with Indian Patent Application No. 202017054203, mailed Jan. 7, 2022, 5 pages.
Kang, et al. "Effect of an osmotic differential on the efficiency of gene transfer by electroporation of fish spermatozoa." Aquaculture 173.1-4 (1999): 297-307. (Year: 1999).
Rieth et al. "Electroporation of bovine spermatozoa to carry DNA containing highly repetitive sequences into oocytes and detection of homologous recombination events." Molecular Reproduction and Development: Incorporating Gamete Research 57.4 (2000): 338-345.
Chamberland et al. "The effect of heparin on motility parameters and protein phosphorylation during bovine sperm capacitation." Theriogenology 55.3 (2001): 823-835. (Year: 2001).
Chan, et al. "Luminescent quantum dots for multiplexed biological detection and imaging." Current opinion in biotechnology 13.1 (2002): 40-46. (Year: 2002).
USPTO, "Non-Final Office Action," issued in connection with U.S. Appl. No. 16/561,146, dated Jan. 21, 2022, 14 pages.
USPTO, "Non-Final Office Action," issued in connection with U.S. Appl. No. 17/496,469, dated Jan. 28, 2022, 13 pages.
USPTO, "Final Office Action," issued in connection with U.S. Appl. No. 17/403,642, dated Mar. 4, 2022, 14 pages.
Australian Office Action, Application No. 2021200818, dated Mar. 4, 2022, 3 pages.
USPTO, "Non-Final Office Action," issued in connection with U.S. Appl. No. 16/741,608, dated Mar. 18, 2022, 12 pages.
USPTO, "Notice of Allowance," issued in connection with U.S. Appl. No. 17/412,789, mailed Mar. 21, 2022, 30 pages.
USPTO, "Notice of Allowance," issued in connection with U.S. Appl. No. 17/458,947, dated Mar. 31, 2022, 30 pages.

(56) References Cited

OTHER PUBLICATIONS

Jun et al. "Detecting and estimating contamination of human DNA samples in sequencing and array-based genotype data." The American Journal of Human Genetics 91.5 (2012): 839-848.
International Searching Authority, "International Search Report and Written Opinion," issued in connection with international Patent Application No. PCT/US21/56094, mailed Mar. 16, 2022, 22 pages.
USPTO, "Notice of Allowance," issued in connection with U.S. Appl. No. 17/496,469, dated May 10, 2022, 54 pages.
China National Intellectual Property Administration, "Notice of Allowance," issued in connection with Chinese Patent Application No. 201480071952.0, dated Mar. 21, 2022, 3 pages.
Notice of Allowance issued in U.S. Appl. No. 17/692,876 on Feb. 1, 2023, 24 pages.
European Patent Office, "European Search Report," issued in connection with European Patent Application No. 22190948.4, mailed Jan. 23, 2023, 10 pages.
European Patent Office, "Intention to Grant Notice," issued in connection with patent application No. 20167363.9, mailed Dec. 15, 2022, 8 pages.
Notice of Allowance issued in U.S. Appl. No. 16/741,608 on Feb. 7, 2023, 22 pages.
Jokinen, Ville, et al. "Durable superhydrophobicity in embossed CYTOP fluoropolymer micro and nanostructures", Colloids and Surfaces A: Physicochemical and Engineering Aspects, vol. 434, 2013, pp. 207-212.
Forsberg et al. "Cassie-Wenzel and Wenzel-Cassie transitions on immersed superhydrophobic surfaces under hydrostatic pressure", Soft Matter, vol. 7, No. 1, 2011, pp. 104-109.
Lu et al. "Photochemical reactions and on-line UV detection in microfabricated reactors", Lab on a Chip, vol. 1, No. 1, 2001, pp. 22-28.
Japan Patent Office, "Office Action," issued in connection with Japanese Patent Application No. 2019-513891, Jun. 17, 2021, 11 pages.
Brazilian Office Action, Application No. BR112019004727-1, mailed Jul. 6, 2021, 4 pages.
Australian Office Action, Application No. 2017323502, mailed Jun. 28, 2021, 6 pages.
China Office Action, Application No. 201780056064.5, mailed Apr. 26, 2021, 8 pages.
China Office Action, Application No. 201780056064.5, mailed Nov. 4, 2020 11 pages.
Europe Office Action, Application No. 17808998.3, mailed Jul. 21, 2020, 8 pages.
Pedreira et al: "Overview of clinical flow cytometry data analysis: recent advances and future challenges", Trends in Biotechnology, Elsevier Publications, Cambridge, GB, vol. 31, No. 7, Jul. 5, 2013, 12 pages.
China Patent Office, "The Third Office Action," issued in connection with China Patent Application No. 201480071952.0, mailed Jul. 23, 2020, 23 pages.
Intellectual Property India, "Examination Report," issued in connection with Indian Patent Application No. 3429/DELNP/2015, mailed Mar. 26, 2018, 6 pages.
European Patent Office, "European Search Report," issued in connection with patent application No. 20167363.9, mailed Jul. 21, 2020, 9 pages.
Japan Patent Office, "Notice of Reasons for Refusal," issued in connection with Japan Patent Application No. 2018-220397, Jul. 31, 2020, 3 pages.
European Patent Office, "Examination Report," issued in connection with European Patent Application No. 16723498.8, mailed Oct. 12, 2020, 6 pages.
European Patent Office, "European Search Report," issued in connection with European Patent Application No. 14168200.5, mailed Mar. 20, 2015, 12 pages.
European Patent Office, "European Search Report," issued in connection with European Patent Application No. 17172322.4, mailed Aug. 24, 2017, 8 pages.
European Patent Office, "European Search Report," issued in connection with European Patent Application No. 15160613.4, mailed Jul. 24, 2015, 14 pages.
European Patent Office, "Communication pursuant to Article 94(3) EPC," issued in connection with European Patent Application No. 17172322.4, mailed Aug. 14, 2018, 5 pages.
European Patent Office, "Communication pursuant to Article 94(3) EPC," issued in connection with European Patent Application No. 11193936.9, mailed Dec. 11, 2015, 3 pages.
European Patent Office, "Communication pursuant to Article 94(3) EPC," issued in connection with European Patent Application No. 15160613.4, mailed Jul. 11, 2016, 4 pages.
Hori et al., "Cell fusion by optical trapping with laser-involves contacting different cells with each other then imparting high voltage pulse to cells," WPI/Thompson, Dec. 27, 1991, Abstract, 1 page.
Japan Patent Office, "Notification of Reasons for Refusal," issued in connection with Japanese Patent Application No. 2016-185743, mailed Jul. 3, 2018, 4 pages.
Japan Patent Office, "Final Notification of Reasons for Rejection," issued in connection with Japanese Patent Application No. 2011-256171, mailed Oct. 28, 2014, 5 pages.
Japan Patent Office, "Decision for Grant," issued in connection with Japanese Patent Application No. 2015-091320, mailed May 9, 2017, 7 pages.
Japan Patent Office, "Final Notification of Reasons for Rejection," issued in connection with Japanese Patent Application No. 2015-091320, mailed Mar. 22, 2016, 22 pages.
Japan Patent Office, "Notification of Reasons for Refusal," issued in connection with Japanese Patent Application No. 2016-185743, mailed Jul. 26, 2017, 2 pages.
Smith et al., "Inexpensive Optical Tweezers for Undergraduate Laboratories," Am. J. Phys., vol. 67, No. 1, Jan. 1999, 10 pages.
Takayama et al., "Patterning Cells and Their Environments Using Multiple Laminar Fluid Flows in Capillary Networks," Proceedings of National Academy of Sciences, vol. 96, 1999, 4 pages.
Guéron et al., Excited states of nucleic acids. Edited by Ts'o, P. O. P., & Eisinger, J. Basic principles in nucleic acid chemistry. New York: Academic Press. pp. 311-387. 1974.
Japan Patent Office; "Notice of Reasons for Refusal," issued in connection with Japanese Patent Application No. 2019-088655, mailed Feb. 18, 2020, 5 pages.
International Preliminary Report on Patentability corresponding to International Patent Application No. PCT/US2013/050669, mailed Jan. 28, 2016, 15 pages.
Supplementary European Search Report for Application No. 13889551.1, dated May 22, 2017, 12 pages.
State Intellectual Property Office of People's Republic of China, "Second Office Action," issued in connection with Chinese Patent Application No. 201380079634.4, Jun. 4, 2018, 14 pages.
Japan Patent Office, "Notice of Reasons for Rejection," issued in connection with Japanese Patent Application No. 2017-168904, Jul. 6, 2018, 3 pages.
State Intellectual Property Office of People's Republic of China, "Third Office Action," issued in connection with Chinese Patent Application No. 201380079634.4, Nov. 1, 2018, 20 pages.
Japanese Office Action for Application No. 2016-527978 dated Mar. 24, 2017, 6 pages.
State Intellectual Property Office of People's Republic of China, "First Office Action," issued in connection with Chinese Patent Application No. 201380079634.4, Jul. 28, 2017, 18 pages.
Indian Patent Application No. 3425/DELNP/2015 Pre-Grant Opposition, mailed Dec. 4, 2020, 138 pages.
Indian Patent Application No. 3425/DELNP/2015 Pre-Grant Opposition, mailed Jul. 21, 2020, 59 pages.
Indian Patent Application No. 3425/DELNP/2015 Pre-Grant Opposition, mailed Jul. 21, 2020, 96 pages.
Indian Patent Application No. 3425/DELNP/2015 Pre-Grant Opposition, mailed Jul. 2, 2020, 137 pages.
Lee et al., The potential of a dielectrophoresis activated cell sorter (DACS) as a next generation cell sorter. Micro and Nano Syst Lett. 2016;4:2, 10 pages.

(56) References Cited

OTHER PUBLICATIONS

Maser et al., Nanoparticle injector for photonic manipulators using dielectrophoresis. AIP Advances 9.6 (2019):065109, 8 pages.
Morgan et al., Separation of Submicron Bioparticles by Dielectrophoresis. Biophysical Journal. vol. 77, 1999, pp. 516-525.
Sutera et al., The history of Poiseuille's law. Annual Review of Fluid Mechanics, 25.1 (1993): pp. 1-20.
USPTO, "Final Office Action," issued in connection with U.S. Appl. No. 16/741,608, dated Oct. 21, 2021, 11 pages.
USPTO, "Non-Final Office Action," issued in connection with U.S. Appl. No. 17/403,642, dated Nov. 29, 2021, 13 pages.
Australian Office Action, Application No. 2017323502, dated Oct. 22, 2021, 6 pages.
Intellectual Property India, "Examination Report," issued in connection with Indian Patent Application No. 201917009874, mailed Nov. 25, 2021, 6 pages.
USPTO, "Final Office Action," issued in connection with U.S. Appl. No. 16/741,608, dated Jun. 13, 2022, 11 pages.
USPTO, "Non-Final Office Action," issued in connection with U.S. Appl. No. 17/403,642, dated Jul. 13, 2022, 7 pages.
CNIPA, "First Office Action," issued in connection with Chinese Patent Application No. 202080028183.1, mailed Jul. 6, 2022, 21 pages.
National Institute of Industrial Property (INPI) Argentina, "Examination Report," issued in connection with Argentina Patent Application No. 20190101378, mailed Apr. 19, 2023, 8 pages.
China National Intellectual Property Administration, "Decision of Rejection," issue in connection with Chinese Patent Application No. 202080028183.1, mailed Jun. 7, 2023, 23 pages.
USPTO, "Non-Final Office Action," issued in connection with U.S. Appl. No. 17/164,710, dated Jun. 26, 2023, 13 pages.
State Intellectual Property Office of People's Republic of China, "First Office Action," issued in connection with Chinese Patent Application No. 2018801002551, Jan. 26, 2024, 8 pages.
USPTO, "Non-Final Office Action," issued in connection with U.S. Appl. No. 17/525,125, mailed Mar. 7, 2024, 15 pages.
Thermofisher, Optics of a Flow Cytometer, Sep. 2020, ThermoFisher, https://www.thermofisher.com/us/en/home/life-science/cell-analysis/cell-analysis-learning-center/molecular-probes-school-of-fluorescence/flow-cytometry-basics/flow-cytometry-fundamentals/optics-flow-cytometer.html (Year: 2020), 76 pages.
De Novo, Flow Cytometery: a basic introduction, Sep. 2019, De Novo, Chapter 2: The Flow cytometer, https://flowbook.denovosoftware.com/chapter-2-flow-cytometer (Year: 2019), 10 pages.
Al-Holy et al., "The Use of Fourier Transform Infrared Spectroscopy to Differentiate *Escherichia coli* O157:H7 from Other Bacteria Inoculated Into Apple Juice," Food Microbiology, vol. 23, 2006, 162-168.
Alberts et al., "Molecular Biology of the Cell, 5th edition," New York: Garland Science, 2008, p. 1293.
Barcot et al., "Investigation of Spermatozoa and Seminal Plasma by Fourier Transform Infrared Spectroscopy," Applied Spectroscopy, vol. 61, No. 3, Mar. 2007, pp. 309-313.
Bassan et al; "Reflection Contributions to the Dispersion Artefact in FTIR Spectra of Single Biological Cells," Analyst, vol. 134, Apr. 9, 2009, pp. 1171-1175.
Bassan et al; "Resonant Mie Scattering in Infrared Spectroscopy of Biological Materials-Understanding the Dispersion Artefact," Analyst, vol. 134, 2009, pp. 1586-1593.
Bassan et al; "Resonant Mie Scattering {RMieS} Correction of Infrared Spectra From Highly Scattering Biological Samples," Analyst, vol. 135, No. 2, Feb. 2010, pp. 268-277.
Belkin et al.; "Intra-Cavity Absorption Spectroscopy with Narrow-Ridge Microfluidic Quantum Cascade Lasers," Optics Express, vol. 15, No. 18, Sep. 3, 2007, pp. 11262-11271.
Boustany et al.; "Microscopic Imaging and Spectroscopy with Scattered Light," Annual Review of Biomedical Engineering, vol. 12, 2010, pp. 285-314.
Chan et al.; "Nondestructive Identification of Individual Leukemia Cells by Laser Trapping Raman Spectroscopy," Analytical Chemistry, vol. 80, No. 6, Mar. 15, 2008, 8 pages.
Chan et al.; "Label-Free Biochemical Characterization of Stem Cells Using Vibrational Spectroscopy," Journal of Biophotonics vol. 2, No. 11, Aug. 5, 2009, pp. 656-668.
Chan et al.; "Label-Free Separation of Human Embryonic Stem Cells (hESCs) and their Cardiac Derivatives using Raman Spectroscopy," Lawrence Livermore Journal, LLNL-JRNL-406938, Sep. 11, 2008, 30 pages.
Chen et al,; "Synchrotron Infrared Measurements of Protein Phosphorylation in Living Single PC12 Cells during Neuronal Differentiation," Analytical Chemistry, vol. 84, 2012, pp. 4118-4125.
Cheng et al., "Laser-Scanning Coherent Anti-Stokes Raman Scattering Microscopy and Applications to Cell Biology," Biophysical Journal, vol. 83, Jul. 2002, pp. 502-509.
Cho et al., "Passively Driven Integrated Microfluidic System for Separation of Motile Sperm," Analytical Chemistry, vol. 75, Apr. 1, 2003, Abstract.
Genzen et al. "Laboratory-developed tests: a legislative and regulatory review." Clinical chemistry 63.10 (2017): 10 pages.
Cho et al., "A microfluidic device for separating motile sperm from nonmotile sperm via inter-streamline crossings," 2nd Annual International IEEE-EMBS Special Topic Conference on Microtechnologies in Medicine and Biology. Proceedings (Cat. No.02EX578), 2002, pp. 156-159, doi: 10.1109/MMB.2002.1002304.
Cleary et al., "Infrared Surface Plasmon Resonance Biosensor," OSA Biomed, Miami, Florida, Apr. 2010, 11 pages.
Dousseau et al., "On the Spectral Subtraction of Water from the FT-IR Spectra of Aqueous Solutions of Proteins," Applied Spectroscopy, vol. 43, No. 3, 1989, pp. 538-542.
Downes et al., "Optical Spectroscopy for Noninvasive Monitoring of Stem Cell Differentiation," Journal of Biomedicine and Biotechnology, vol. 2010, Article ID 101864, 2010, 10 pages.
Ege, "Organic Chemistry: Structure and Reactivity," Fifth Edition, Boston, MA, Houghton Mifflin Company, 2004, pp. 453-457.
European Patent Office, "Extended European Search Report," issued in connection with European Patent Application No. 11841869.8, mailed Feb. 15, 2018, 9 pages.
Fu et al., "A Microfabricated Fluorescence-Activated Cell Sorter," Nature Biotechnology, vol. 17, Nov. 1999, pp. 1109-1111.
Green et al., "Flow Cytometric Determination of Size and Complex Refractive Index for Marine Particles: Comparison with Independent and Bulk Estimates," Applied Optics, vol. 42, No. 3, Jan. 20, 2003, pp. 526-541.
Harvey et al., "Discrimination of Prostate Cancer Cells by Reflection Mode FTIR Photoacoustic Spectroscopy," The Analyst, vol. 132, 2007, pp. 292-295.
Herzenberg et al., "Fluorescence-activated Cell Sorting," Scientific American, vol. 234, Mar. 15, 1976, pp. 108-117.
Holman et al., "Synchrotron-Based FTIR Spectromicroscopy: Cytotoxicity and Heating Considerations," Journal of Biological Physics, vol. 29, 2003, pp. 275-286.
Holman et al., "IR Spectroscopic Characteristics of Cell Cycle and Cell Death Probed by Synchrotron Radiation Based Fourier Transform IR Spectromicroscopy," Biopolymers (Biospectroscopy) vol. 57, 2000, pp. 329-335.
Holman et al., "Tracking Chemical Changes in a Live Cell: Biomedical Applications of SR-FTIR Spectromicroscopy," Lawrence Berkeley National Laboratory, http://escholarship.org/uc/item/9k185794, Berkeley, CA Jul. 25, 2002, 34 pages.
Huser et al., "Raman Spectroscopy of DNA Packaging in Individual Human Sperm Cells Distinguishes Normal From Abnormal Cells," Journal of Biophotonics, vol. 2, No. 5, 2009, pp. 322-332.
Intel, "Intel C-bank Tunable Laser, Performance and Design," White Paper, May 2003, 14 pages.
International Searching Authority, "International Search Report and Written Opinion," International Patent Application No. PCT/US2013/041123, mailed Aug. 19, 2013, 12 pages.
International Search Authority, "International Preliminary Report on Patentability," International Patent Application No. PCT/US2011/061046, mailed May 30, 2013, 7 pages.

(56) References Cited

OTHER PUBLICATIONS

International Searching Authority, "International Preliminary Report on Patentability," International Patent Application No. PCT/US2013/041123, Nov. 18, 2014, 7 pages.

Japan Patent Office, "Office Action," issued in connection with Japanese Patent Application No. 2013-539983, Jul. 8, 2015, 6 pages.

Japan Patent Office, "Office Action," issued in connection with Japanese Patent Application No. 2013-539983, Jul. 2, 2016, 6 pages.

Japan Patent Office, "Office Action," issued in connection with Japanese Patent Application No. 2016-198323, Oct. 2, 2017, 3 pages.

Japan Patent Office, "Office Action," issued in connection with Japanese Patent Application No. 2016-198323, Jul. 25, 2018, 9 pages.

Lee et al., "DFB Quantum Cascade Laser Arrays," IEEE Journal of Quantum Electronics, vol. 45, No. 5, May 2009, pp. 554-565.

Libbus et al., "Incidence of Chromosome Aberrations in Mammalian Sperm Stained with Hoechst 33342 and UV-Laser Irradiated During Flow Sorting," Mutation Research, vol. 182, 1987, pp. 265-274.

Malone, Jr., "Infrared Microspectroscopy: A Study of the Single Isolated Bread Yeast Cell," Thesis, The Ohio State University, 2010, 162 pages.

Meister et al., "Confocal Raman Microspectroscopy as an Analytical Tool to Assess the Mitochondrial Status in Human Spermatozoa," Analyst, vol. 135, 2010, pp. 1370-1374.

Miyamoto et al., "Label-free Detection and Classification of DNA by Surface Vibration Spectroscopy in Conjugation with Electrophoresis," Applied Physics Letters, vol. 86, No. 053902, 2005, 3 pages.

Mohlenhoff et al., "Mie-Type Scattering and Non-Beer-Lambert Absorption Behavior of Human Cells in Infrared Microspectroscopy," Biophysical Journal, vol. 88, May 2005, pp. 3635-3640.

Montag et al., "Laser-induced Immobilization and Plasma Membrane Permeabilization in Human Spermatozoa," Human Reproduction, vol. 15, No. 4, 2000, pp. 846-852.

Mourant et al., "Methods for Measuring the Infrared Spectra of Biological Cells," Physics in Medicine and Biology, vol. 48, 2003, pp. 243-257.

Van Munster, "Interferometry in Flow to Sort Unstained X-and Y-Chromosome-Bearing Bull Spermatozoa," Cytometry, vol. 47, 2002, pp. 192-199.

Rajagopalan et al., "Aneuploidy and Cancer," Nature, vol. 432, Nov. 2004, pp. 338-341.

Ropcke et al., "Application of Mid-Infrared Tuneable Diode Laser Absorption Spectroscopy to Plasma Diagnostics: A Review," Plasma Sources Science and Technology, vol. 15, 2006, S148-S168.

Schaden et al., "Quantum Cascade Laser Modulation for Correction of Matrix-Induced Background Changes in Aqueous Samples," Applied Physics B, vol. 86, 2007, pp. 347-351.

Sandt et al., "Identification of Spectral Modifications Occurring during Reprogramming of Somatic Cells," PLoS One, vol. 7, Issue 4, e30743, Apr. 2012, 7 pages.

USPTO, "Notice of Allowance," issued in connection with U.S. Appl. No. 16/852,303, mailed Sep. 20, 2023, 31 pages.

European Patent Office, "Communication pursuant to Article 94(3) EPC," issued in connection with European Patent Application No. 17808998.3, mailed Sep. 15, 2023, 4 pages.

European Patent Office, "European Search Report," issued in connection with patent application No. 20913158.0, mailed Sep. 20, 9 pages.

European Patent Office, "European Search Report," issued in connection with patent application No. 23169267.4 mailed Jul. 14, 2023, 5 pages.

Brazilian Office Action, Application No. BR112021012000-9, mailed Aug. 16, 2023, 4 pages.

Japan Patent Office, "Office Action," issued in connection with Japanese Patent Application No. 2022-540313, May 7, 2024, 3 pages.

USPTO, "Final Office Action," issued in connection with U.S. Appl. No. 17/416,727, mailed May 2, 2024, 11 pages.

Maxwell, W.M.C & Johnson, L.A.; Chlortetracycline analysis of boar spermatozoa after incubation, flow cytometric sorting, cooling, or cryopreservation; Molecular Reproduction Development, 46: 408-419 (1997).

Johnson, L.A. et al.; Artificial Insemination of Swine: Fecundity of boar semen stored in Beltsville TS (BTS), Modified Modena (MM), or MR-A and inseminated on one, three and four days after collection; Reproduction in domestic Animals, vol. 23, Issue 2, pp. 49-55 (1988).

Stap, J. et al.; Improving the resolution of cryopreserved X- and Y-Sperm during DNA flow cytometric analysis with the addition of Percoll to quench the fluorescence of dead sperm; Journal of Animal Science, 76: 1896-1902 (1998).

De Leeuw, F.E. et al.; Effects of various cryoprotective agents and membrane-stabilizing compounds on bull sperm membrane integrity after cooling and freezing; Cryobiology, 30, 32-44 (1993).

Fievet et al., ART-Deco: easy tool for detection and characterization of cross-contamination of DNA samples in diagnostic next-generation sequencing analysis, European Journal of Human Genetics, vol. 27, No. 5, Jan. 25, 2019, pp. 792-800.

European Patent Office, "Extended European Search Report," issued in connection with patent application 21883920.7 dated Sep. 9, 2024.

European Patent Office, "Extended European Search Report," issued in connection with patent application 21895392.5 dated Sep. 4, 2024.

China National Intellectual Property Administration, "Second Office Action," issued in connection with Chinese Patent Application No. 202080028183.1, mailed Jan. 13, 2023, 23 pages.

Notice of Allowance issued in U.S. Appl. No. 17/851,319 on Feb. 15, 2023, 52 pages.

USPTO, "Final Office Action," issued in connection with U.S. Appl. No. 16/852,303, dated May 27, 2022, 48 pages.

USPTO, "Non-Final Office Action," issued in connection with U.S. Appl. No. 16/279,430, dated May 23, 2022, 14 pages.

European Patent Office, "Examination Report," issued in connection with patent application No. 20167363.9, mailed Mar. 22, 2022, 4 pages.

European Patent Office, "Examination Report," issued in connection with patent application No. 19182993.6, mailed May 10, 2022, 8 pages.

International Search Report and Written Opinion for Application Serial No. PCT/US2021/059148, dated May 4, 2022, 15 pages.

European Patent Office, "Communication under Rule 71(3) EPC," issued in connection with European Patent Application No. 16723498.8, mailed May 18, 2022, 54 pages.

IP Australia, "Notice of Acceptance for Patent Application," issued in connection with Australian Patent Application No. 2021200818, mailed Jun. 1, 2022, 3 pages.

USPTO, "Non-Final Office Action," issued in connection with U.S. Appl. No. 17/692,876, dated Sep. 19, 2022, 21 pages.

USPTO, "Notice of Allowance," issued in connection with U.S. Appl. No. 17/403,642, mailed Sep. 29, 2022, 24 pages.

Brazilian Office Action, Application No. BR112019004727-1, mailed Mar. 20, 2023, 6 pages.

USPTO "Final Office Action," issued in connection with U.S. Appl. No. 16/852,303, mailed May 1, 2023, 33 pages.

European Patent Office, "European Search Report," issued in connection with patent application No. 21895392.5, mailed Nov. 26, 2024, 10 pages.

China National Intellectual Property Administration, "Second Office Action," issued in connection with Chinese Patent Application No. 202080091173.2, mailed Jan. 8, 2025, 25 pages.

USPTO "Final Office Action," issued in connection with U.S. Appl. No. 17/507,662, mailed Jan. 6, 2025, 21 pages.

(56) References Cited

OTHER PUBLICATIONS

USPTO, "Notice of Allowance," issued in connection with U.S. Appl. No. 29/867/647, mailed Jan. 29, 2025, 16 pages.

* cited by examiner

SYSTEMS AND METHODS FOR PARTICLE FOCUSING IN MICROCHANNELS

CROSS-REFERENCES TO RELATED APPLICATIONS

This application is a continuation and claims benefit of U.S. patent application Ser. No. 16/419,756 filed May 22, 2019, which is a non-provisional and claims benefit of U.S. Provisional Application No. 62/675,512 filed May 23, 2018, the specification(s) of which are incorporated herein in their entirety by reference.

BACKGROUND OF THE INVENTION

Flow cytometers function by passing individual particles, such as cells, within a stream of fluid past a detector, which measures certain characteristics of each particle and takes actions based on that evaluation. To do that, the flow cytometer must regulate the flow of the sample so that the particles in the sample move into a substantially single-file particle stream, which enables each particle to be measured individually by the detector.

One area where flow cytometers have found practical use is in connection with sexing sperm cells, such as bovine sperm, according to sperm cell characteristics for use by the animal reproduction industry to preselect the sex of animal offspring. The most common method for sexing sperm cells is to discriminate based on DNA content. In this context, sperm is combined with an extender and a luminescent dye to stain the DNA inside the sperm cell. The stained sperm cells are then placed in a sample fluid which is introduced into a channel of a microfluidic chip that uses focusing techniques to orient the sperm cell into a substantially single-file stream. After being properly oriented, the sperm cells are illuminated with a light source (e.g., a laser), which excites the luminescent dye in the DNA, giving off a fluorescent luminescence which is detected by a detector (e.g., a photomultiplier tube ("PMT") or an avalanche photodiode (APD)). A sperm containing the X chromosome has more DNA than a Y chromosome-bearing sperm, resulting in the X chromosome-bearing sperm producing more luminescence in response to the detection light source. The detected luminescence is monitored and the system takes selective action, e.g., sorting or killing non-selected sexed sperm with a kill laser, on the individual sperm cells to achieve an end product with the desired characteristics, e.g., a sample with a high concentration of either X or Y chromosome-bearing sperm. For example, if female calves are desired (e.g., for dairy production), then the system is calibrated to collect cells having detected luminescence parameters that are what would be expected of an X chromosome-bearing sperm cell. Alternatively, if male calves are desired (e.g., for beef production), then the system is calibrated to collect cells having detected luminescence parameters that are what would be expected of a Y chromosome-bearing sperm cell.

Sperm cells may also be distinguished based on DNA content by other methods that do not utilize a DNA dye. For example, U.S. Pat. No. 8,941,062 describes systems and methods of cytometry involving presenting a single sperm cell to at least one laser source configured to deliver light to the sperm cell in order to induce bond vibrations in the sperm cell DNA and detecting the signature of the bond vibrations. Sperm cells may also be analyzed and distinguished based on the presence or absence of cell surface markers or protein, through binding of a fluorescently labeled ligand, such as an antibody. Other methods for discriminating sperm cells may utilize other features of sperm cells, such as mass or volume, to differentiate between those that contain X-chromosomes and those that contain Y-chromosomes. These discrimination and detection methods similarly permit the cells to be selectively differentiated and for the sample to be sexed.

Sexing techniques include a variety of methods to sort, separate, eliminate, or inactivate unwanted cells. For example, so-called laser kill methods involve exposure of particular cells to a laser with sufficient energy to inactivate the cells. Cells may also be separated into populations through sorting, for example, through droplet formation and deflection as described in U.S. Pat. No. 5,700,692.

In cell discrimination techniques, including sperm cell sexing applications, proper orientation, ordering, and location of the cells within the microfluidic system is essential to effective operation. For example, positioning and orientation are both essential for being able to effectively detect the difference in fluorescence of X- and Y-chromosome bearing sperm cells stained with a DNA-intercalating dye, as both the positioning of cells within the beam of the detection laser and the orientation of the cells with respect to the detector significantly impact the amount of fluorescence detected. Alterations in the fluorescence, in turn, directly affect the ability to distinguish differences in the fluorescence signal between X-chromosome and Y-chromosome bearing cells. Further, during the sexing process, the various techniques used depend on the ability to accurately locate the cells within the fluid stream. For example, in laser kill sexing, the kill laser is narrowly focused in a particular spot and requires that the cells be positioned properly for the exposure to be effective to be inactivating the cell. Positioning of cells within the flow stream (i.e., up, down, left, and right, with respect to the axis of travel) and ordering (i.e., the distance between cells along the axis of travel) are also important for sorting techniques (i.e., droplet formation and deflection, thermal bubble sorting, etc.). Ordering of cells in a sample flow may be non-deterministic (i.e., follows a Poisson distribution) or deterministic (i.e., spacing). Ordering, therefore, refers to control of cell incidence in the sample flow.

Hydrodynamic focusing has been utilized to align cells, including sperm cells, in flow cytometry applications for many years, but it may have drawbacks. First, hydrodynamic focusing may involve multiple fluid streams, including one or more sheath fluid streams. Sheath fluid is consumable in the flow cytometric process and can be a significant cost. In addition, hydrodynamic focusing may involve microfluidic chips being designed and produced with complex sample and sheath flow channels, leading to relatively high costs for the microfluidic chips. The number of flow controllers required for each number of fluid inlets may also impact the cost. Further, hydrodynamic focusing relies on a consistent flow rate of the sheath flow, and fluctuations in flow rate, for example, due to a loss of pressure or occlusion of a sheath channel, can have adverse effects on cytometer performance.

Inertial flow focusing has been utilized for cell types, such as white blood cells and cancer cells. Those cells are significantly larger than sperm cells and are uniformly shaped (i.e., substantially spherical). In contrast, sperm cells are significantly smaller, non-uniform, and have a tail. As a result, the balance of forces acts differently on sperm cells than on other cell types.

BRIEF SUMMARY OF THE INVENTION

Certain embodiments of the claimed invention are summarized below. These embodiments are not intended to limit the scope of the claimed invention, but rather serve as brief descriptions of possible forms of the invention. The invention may encompass a variety of forms which differ from these summaries.

According to an embodiment, particle focusing is achieved using a microchannel, wherein the ratio of the particle diameter (a) to the hydraulic diameter of the channel (Dh), defined by the formula a/Dh, is between about 0.03 and about 0.06, and/or wherein the ratio of curvature (radius "r" or "critical parameter") to the hydraulic diameter of the channel, defined by the formula $2ra^2/Dh^3$, is less than about 0.03.

As used herein, "focusing" refers to the spatial organization of cells into a desired formation, in particular, into a defined spatial width with reference to an axis along which the cells are moving in a microfluidic channel, and/or relative to a defined point of reference, such as the detection or kill laser focus point or both). In an embodiment, a focused flow of cells will all be within 3-5 times a given cell dimension (i.e., width, height, or length) of the center line of the axis of travel. In other embodiments, a focused flow of cells will all be within 2-3 times the cell dimension and in other embodiments within 1-2 times the cell dimensions.

Upon entering the microfluidic system, cells are initially unfocused (i.e., not within the desired spatial parameters); various forces can act on the cells within the flow stream to bring them within the desired spatial parameters (i.e., the cells are focused).

Other aspects will be apparent to one of ordinary skill in the art upon review of the description and exemplary aspects and embodiments that follow.

BRIEF DESCRIPTION OF THE SEVERAL VIEWS OF THE DRAWING(S)

For the purpose of illustrating the disclosure, there are depicted in the drawings certain features of the aspects and embodiments of the disclosure. However, the disclosure is not limited to the precise arrangements and instrumentalities of the aspects depicted in the drawings.

FIG. 1A shows a repetitively curved portion of a microchannel according to certain aspects of an embodiment of the present disclosure. FIG. 1B shows a modified inertial focusing design according to certain aspects of an embodiment of the present disclosure. FIG. 1C shows a different modified inertial focusing design according to certain aspects of an embodiment of the present disclosure. FIG. 1D shows an inertial focusing design according to certain aspects of an embodiment of the present disclosure.

DETAILED DESCRIPTION OF THE INVENTION

Figure 1A:

Before continuing to describe various aspects and embodiments in further detail, it is to be understood that this disclosure is not limited to specific compositions or process steps and may vary. As used in this specification and the appended claims, the singular form "a," "an," and "the" include plural referents unless the context clearly dictates otherwise. Ranges expressed herein are inclusive.

An embodiment of the microfluidic chip may be used in connection with sexing sperm cells such as bovine sperm, for example. In particular, the chip may be used in an apparatus that uses flow cytometry for sexing sperm cells according to DNA characteristics for use by the animal reproduction industry to preselect the sex of animal offspring. Briefly, sperm is combined with an extender and a luminescent dye to stain the DNA inside the sperm cell. The dye-stained sperm cells are then placed in a sample fluid which is introduced into a channel of the microfluidic chip. As the sperm cells are not spherical, the microfluidic chip substantially orients the sperm cells to reduce differences in detecting luminescence that may otherwise be caused by differences in the cell's orientation with respect to the detector.

The oriented sperm cells are then illuminated with a light source (e.g., detection laser), which excites the luminescent dye in the DNA, giving off a fluorescent luminescence which is detected by a detector (e.g., a photomultiplier tube (PMT) or an avalanche photodiode (APD)). The sperm containing the X chromosome has more DNA than the Y chromosome-bearing sperm, resulting in the X chromosome-bearing sperm producing more luminescence in response to the original illumination. The difference in total DNA content varies by species; for example in *Bos taurus*, the X chromosome has approximately 3.8% more DNA than the Y chromosome, which results in approximately a 3.8% difference in fluorescence.

In order to determine which cells to kill, an output signal of the detector representing the amplitude of detected luminescence is monitored. When the detected luminescence value exceeds a set threshold value, an event is considered to have begun. The luminescence value is monitored, and when an inflection point or "peak" is detected, the peak is considered to be the center of the cell, and the peak luminescence value is considered the luminescence value for that cell. If more than one peak is detected in a single event, the peak with the greatest amplitude is considered to be the center of the cell and the peak luminescence value is considered to be the luminescence value for that cell and the other peaks are disregarded.

The luminescence value for each sperm cell is compared to a gate, which has been previously defined, to determine whether the cell displays the desired luminescence. For example, if female calves are desired (e.g., for dairy production), then the gate is selected to include cells having detected luminescence parameters that are what would be expected of an X chromosome-bearing sperm cell. Alternatively, if male calves are desired (e.g., for beef production), then the gate is selected to include cells having detected luminescence parameters that are what would be expected of a Y chromosome-bearing sperm cell.

After passing through the detection laser and having their luminescence detected, the stained sperm cells, still in the stream, then pass into the kill zone. A second light source, e.g., the kill laser, is selectively activated to kill cells that fall outside of the selected gate as they pass through the kill zone.

In other embodiments, particle focusing according to the present invention can be utilized to distinguished sperm cells based on DNA content by methods that do not utilize a DNA dye. For example, U.S. Pat. No. 8,941,062 describes systems and methods of cytometry involving presenting a single sperm cell to at least one laser source configured to deliver light to the sperm cell in order to induce bond vibrations in the sperm cell DNA and detecting the signature of the bond vibrations. In other embodiments, sperm cells may be analyzed and distinguished based on the presence or absence of cell surface markers or protein, through binding of a fluorescently labeled ligand, such as an antibody. Other methods for discriminating sperm cells may utilize other features of sperm cells, such as mass or volume, to differentiate between those that contain X-chromosomes and those that contain Y-chromosomes. These discrimination and detection methods similarly permit the cells to be selectively differentiated and for the sample to be sexed. In further embodiments, sperm cells may be differentiated based on characteristics other than sex. For example, sperm cells may be differentiated on the basis of the presence or absence of a genetic marker or combination of markers, or cell surface protein.

In other embodiments, particle focusing as described herein may be used for semen sexing techniques to sort, separate, eliminate, or inactivate unwanted cells. For example, so-called laser kill methods involve exposure of particular cells to a laser with sufficient energy to inactivate the cells. Cells may also be separated into populations through sorting, for example, through droplet formation and deflection as described in U.S. Pat. No. 5,700,692. Other sorting techniques for use in the present invention include, for example, bubble sort, acoustic, photonic pressure, holographic laser steering, and optical trapping.

The microfluidic chip according to the present design uses a repetitively curved microchannel for ordering and focusing particles in sample fluid mixture. The chip may be composed of one or more substrates in which the channel, or a portion of the channel, is formed. The substrate may be composed of one or more layers. The channel is a three-dimensional structure within the assembled one or more layers of the one or more substrates. In one embodiment, the chip may include two layers, a bottom layer and a top layer, that are stacked together to form the chip. In an embodiment, a repetitively curved portion of the microchannel is formed entirely on the bottom layer, while inlets and outlets to the microchannel may be formed on either or both chip layers. In other embodiments, the microchannel may be formed in two or more layers of a substrate, or multiple substrates. The repetitively curved portion consists of a repeating series of identically-shaped turns as is illustrated in FIG. 1

In use, a sample fluid is introduced into the microchannel through a sample inlet. In the context of bovine semen, the sample includes an ejaculate and a buffer. Upon entering the microchannel, the particles are randomly dispersed within the sample fluid. As the sample flows through, the microchannel of the particles are longitudinally ordered such that, upon exiting the curved portion, the particles are aligned longitudinally in a row. The microchannel may include horizontal/lateral and/or vertical tapering downstream of the curved portion to provide additional focusing of the particles before the fluid moves through a detection region (not shown).

Figure 1B:
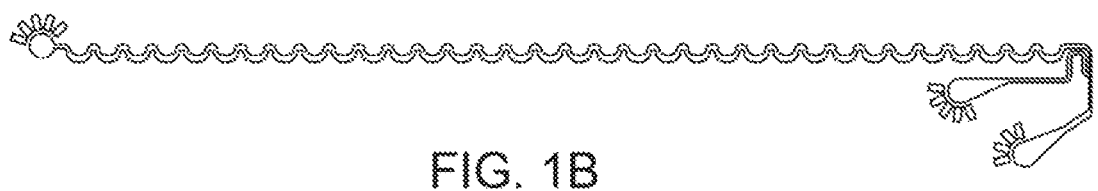
Figure 1C:
Figure 1D:
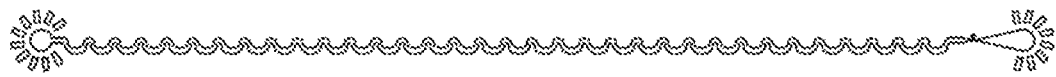
Figure 2A:
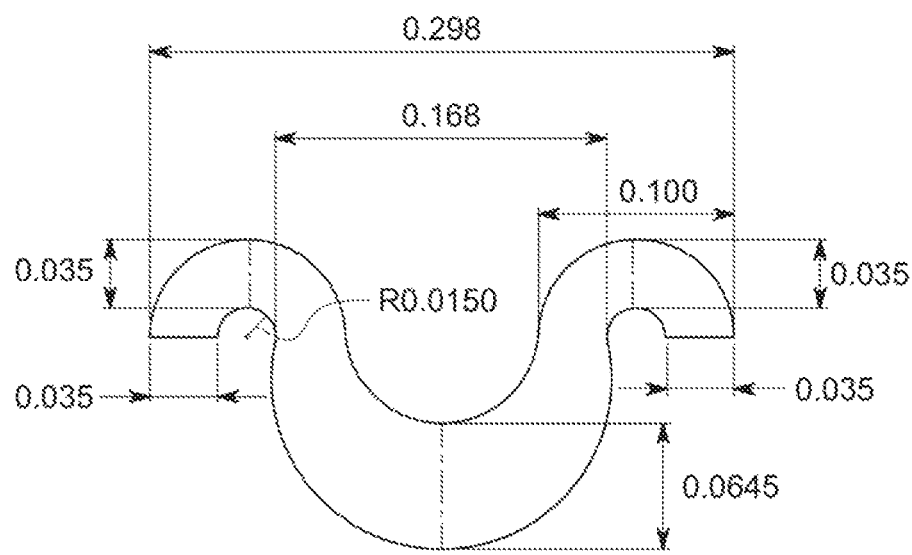
FIGS. 2A and 2B show enlarged views of a curved segment of an embodiment of the microchannel of FIG. 1.
Figure 2B:
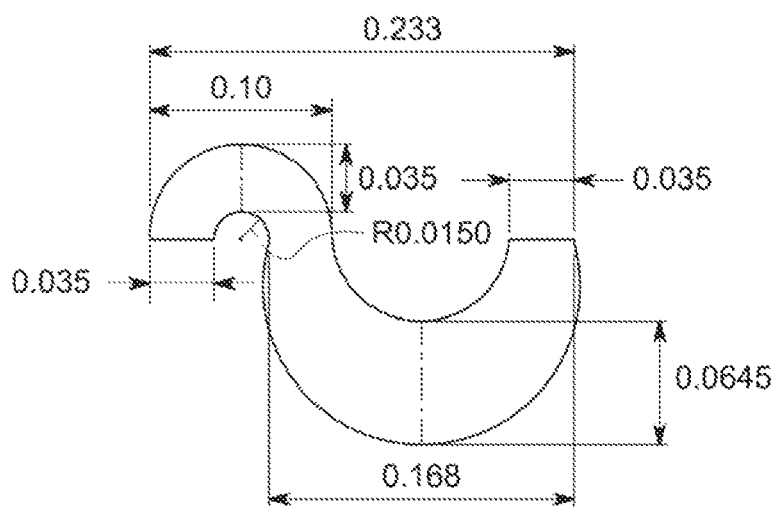
Figure 3A:
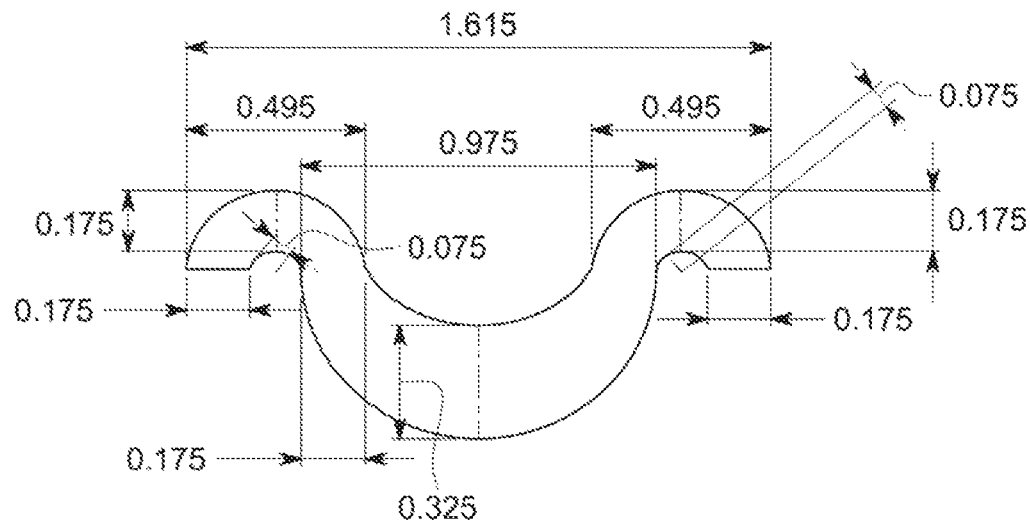
FIGS. 3A and 3B show enlarged views of a curved segment of another embodiment of the microchannel of FIG. 1.
Figure 3B:
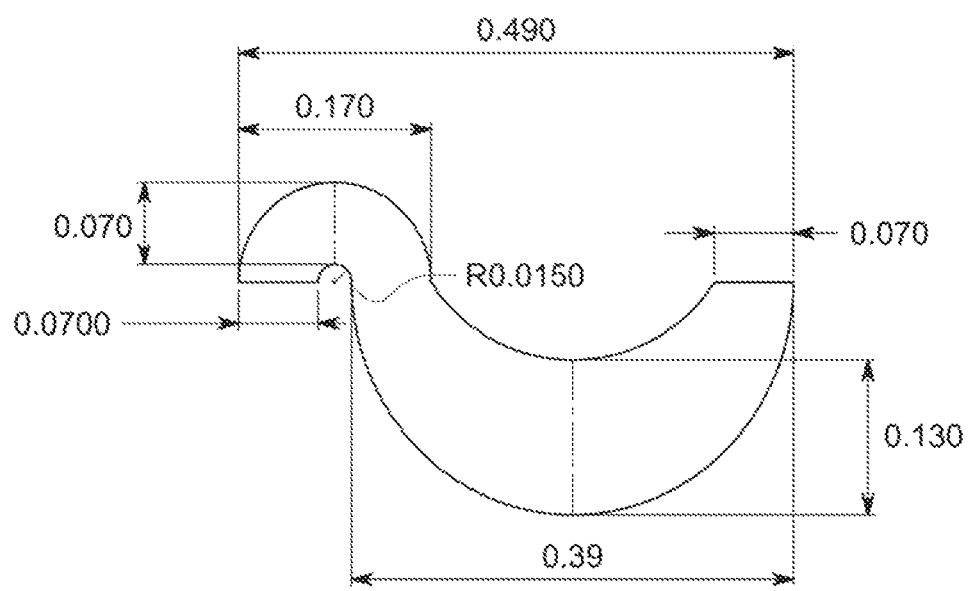

FIGS. 2A and 2B are enlarged views of a curved segment of an embodiment of the microchannel of FIG. 1, FIGS. 3A and 3B are enlarged views of another embodiment of the microchannel of FIG. 1.

The channels depicted above which permit only a single focusing position due to the regulating effect of Dean flows comprise 1.5 turns (FIG. 2A and FIG. 3A) or a single turn (FIG. 2B and FIG. 3B). Referring to FIGS. 2B and 3B, each turn includes a smaller region; the critical parameter is indicated (0.015 mm). In both FIGS. 2 and 3, each turn also includes a larger region (i.e., the lower portion of the turn). The smaller region and larger region are staggered. Together, one smaller region and one larger region constitute a single turn of the microfluidic channel. The turns depicted in FIGS. 2 and 3 are asymmetric, in that, the smaller regions and larger regions are different, and the overall turn is therefore not internally symmetric. In other embodiments, the turn may be symmetric, wherein the left and right sides (i.e., the upper and lower portions of the turn) have the same geometries. In other embodiments, the turns within a focusing channel may include one or more symmetric turns, one or more asymmetric turns, or combinations thereof. In further embodiments, the focusing channels may further include other hydraulic mechanisms to effect the positioning, orientation, and/or ordering of particles within the sample flow.

Figure 4A:
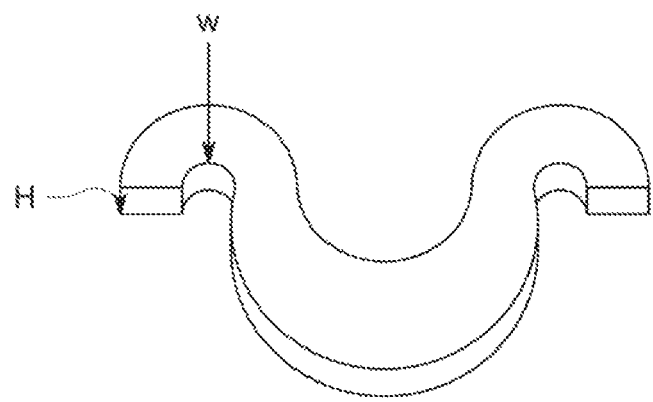
FIGS. 4A and 4B show the critical parameter or curvature radius "r".
Figure 4B:
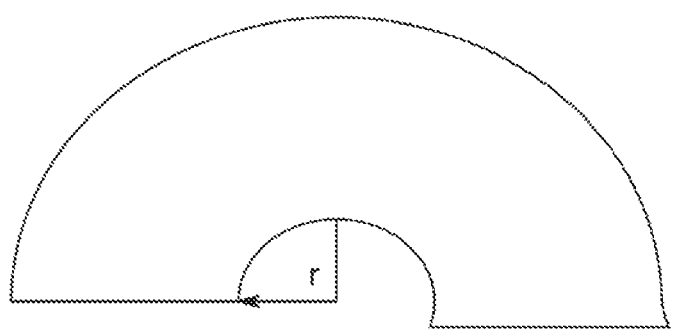

FIGS. 4A and 4B illustrate how to measure the critical parameter "r".

As shown in FIG. 4A, the cross-sectional area is determined by the height (H) and width (W) of the microchannnel at the smaller region of a turn. FIG. 4B shows the determination of the radius of the smaller region of a turn.

According to an aspect, particle focusing is achieved using a repetitively curved microchannel:

wherein the ratio of the particle diameter (a) to the hydraulic diameter of the channel ($D_h$), defined by the formula $a/D_h$ is between about 0.03 and about 0.06, and/or wherein the ratio of curvature (radius "r" or "critical parameter") to the hydraulic diameter of the channel) defined by the formula $2ra^2/Dh^3$ is less than about 0.03.

In another aspect, the particle may be bovine sperm cells. Bovine sperm cells are irregularly shaped and sperm cells are smaller, non-uniform (~3 μm thick×5 μm wide×10 μm long) and have a tail. In this context, the diameter of the cell is considered to be on the order of about 3 μm to about 5 μm. Substantial particle focusing of bovine sperm cells is observed when the microfluidic channel geometries meet one or both of the above conditions. However, if the physical geometries fall outside these ranges, for example, if $a/D_h$ is greater than about 0.06 or less than about 0.03, bovine sperm cells do not focus.

Any number of microfluidic system configurations can be designed to achieve certain specific results and/or properties associated with particle focusing within the various channel geometries. In the examples below, certain properties associated with the systems described herein will now be discussed in more detail. While certain experimental conditions may be discussed in reference to certain properties or parameters, it is to be understood that the properties and parameters are widely applicable to any of the channel geometries.

Example 1 in one aspect, the inertial focusing design (FIG. 1D) was tested in both polydimethylsiloxane (PDMS) and glass at 4 different flow rates. Measurements were taken of core stream width, flat percent, and edge-on percentage, and are shown in Table 1. Figures are shown for PDMS, and where measurements differed when taken in glass chips are shown in parentheses.

Core stream width (e.g., W_68, W_95, W_100) is the measured width of a certain percentage of the core stream, as measured using images taken by a stroboscope of the sample flowing through the microfluidic chip. For instance, W_68 is the measured width of the 68% of the core stream.

Flat percent, which is measured on a stroboscope, is the measurement of cells that are oriented with the broadest cross-section parallel to the top of the channel, and therefore also perpendicular to the detector and ablation laser beam paths.

Edge-on percentage, which is measured on a stroboscope, is the measurement of cells with the narrowest cross-section perpendicular to the top of the channel, and therefore parallel to the laser beam paths.

TABLE 1

| Flow rate | 68% core width | 95% core width | 100% core width | Flat % | Edge-on % |
|---|---|---|---|---|---|
| 250 µL/min | 6-8 µm | 12-16 µm | 24-30 µm | 37-50% (53-68%) | 23-29% (7-13%) |
| 300 µL/min | 4.5-7.5 µm | 9-14 µm | 13-33 µm | 42-50% (58-67%) | 22-27% (5-7%) |
| 350 µL/min | 5-7 µm | 10-12.5 µm | 14-28 µm | 45-62% (52-68%) | 15-21% (6-9%) |
| 400 µL/min | 5-10 µm | 12-20 µm (10-12 µm) | 15-31 µm (18-21 µm) | 42-47% (43-68%) | 22-24% (7-8%) |

Example 2

In another aspect, a modified inertial focusing design (FIG. 1C) was tested. The modified design incorporated an upstream element that includes a curvature in the channel in combination with on-chip dilution to achieve sample focusing in the Z dimension (i.e., top-to-bottom, relative to the direction of travel). The parameters for the curvature of this upstream element were 200 µm radius and 100 µm width (R200W100), 300 µm radius and 100 µm width (R300W75), and 500 µm radius and 100 µm width (R500W100). Dilution was tested at 5%, 10%, 12.5%, and 20% dilution. The inertial focusing portion of the modified design is identical to the inertial focusing design tested in Example 1 and measurements reported in Table 2 include core stream width, flat percent, and edge-on percentage.

TABLE 2

| Curvature dimensions | 68% core width 5/10/12.5/20% dilution (ave.) | 95% core width 5/10/12.5/2% dilution | 100% core width 5/10/12.5/20% dilution | Flat % 5/10/12.5/20% dilution | Edge-on % 5/10/12.5/20% dilution |
|---|---|---|---|---|---|
| R200W100 | 3.9/4.3/3.9/4.0 µm (4.0) | 7.7/8.5/7.9/8.1 µm (8.0) | 13.3/14.1/14.0/13.6 µm (13.8) | 53/53/51/47% (51%) | 11/16/15/19% (15%) |
| R300W75 | —/3.6/3.8/4.0 µm (3.8) | —/7.1/7.5/8 (7.5) | —/10.1/12.4/14.1 µm (12.2) | —/58/54/52% (54%) | —/10/9/7% (8%) |
| R500W100 | 4.2/3.5/6.3/4.8 µm (4.7) | 8.4/7.0/12.5/9.5 µm (9.4) | 18.3/7.8/16.4/12.0 (13.6) | 65/57/58/62% (60%) | 11/8/11/13% (11%) |

Example 3

In another aspect, the different modified design was tested, which incorporated a downstream element that includes a curvature in the channel without any on-chip dilution (FIG. 1B). In another aspect, the secondary region downstream of the inertial focusing channel in this design included a secondary input to potentially adjust the entry point of the cells into the curved section of the drifting element, although this element was not utilized during testing. The data in Table 3 provides the same type of results obtained for the modified and unmodified inertial focusing designs discussed in the previous examples. Measurements were taken using a flow rate of 300 µl/min.

TABLE 3

| 68% core width | 95% core width | 100% core width | Flat % | Edge-on % |
|---|---|---|---|---|
| 8 µm | 16 µm | 20 µm | 50% | 11% |

While illustrative embodiments have been illustrated and described, it will be appreciated that various changes can be made therein without departing from the spirit and scope of the invention.

What is claimed is:

1. A microfluidic chip for focusing a flow of sperm cells suspended in a fluid, the sperm cells having a diameter (a), the microfluidic chip comprising:
   one or more substrates;
   a focusing channel formed in the one or more substrates and spanning a length from an inlet to an outlet for receiving the flow of sperm cells suspended in the fluid, the focusing channel comprising a repetitively curved segment having a hydraulic diameter ($D_h$), wherein:
   a ratio of the cell diameter to the hydraulic diameter of the channel ($a/D_h$) is between about 0.03 and about 0.06;
   a ratio of curvature (critical parameter "r") to the hydraulic diameter ($D_h$) defined by the formula $2ra^2/D_h^3$ is less than about 0.03; and
   the focusing channel comprising a straight portion disposed downstream of the repetitively curved segment.

2. The microfluidic chip of claim 1, wherein an internal geometry of the focusing channel causes the sperm cells to form a focused flow of the sperm cells in the focusing channel.

3. The microfluidic chip of claim 1, wherein the repetitively curved segment comprises one or more symmetrically shaped segments and one or more asymmetrically shaped segments.

4. The microfluidic chip of claim 1, wherein the straight portion comprises a taper.

5. The microfluidic chip of claim 4, wherein the taper comprises a horizontal or lateral tapering.

6. The microfluidic chip of claim 4, wherein the taper comprises a vertical taper.

7. The microfluidic chip of claim 1, further comprising a detection region.

8. The microfluidic chip of claim 1, further comprising a kill zone.

9. A microfluidic chip for focusing a flow of sperm cells suspended in a fluid, the sperm cells having a diameter (a), the microfluidic chip comprising:
  one or more substrates;
  a focusing channel formed in the one or more substrates and spanning a length from an inlet to an outlet for receiving the flow of sperm cells suspended in the fluid, the focusing channel comprising a repetitively curved segment having a hydraulic diameter ($D_h$), wherein:
    a ratio of the cell diameter to the hydraulic diameter of the channel ($a/D_h$) is between about 0.03 and about 0.06;
    a ratio of curvature (critical parameter "r") to the hydraulic diameter ($D_h$) defined by the formula $2ra^2/D_h^3$ is less than about 0.03; and
  an on-chip dilution element upstream of the repetitively curved segment.

10. The microfluidic chip of claim 9, wherein the on-chip dilution element provides for focusing of the flow of sperm cells suspended in the fluid in a Z dimension, top-to-bottom relative to the direction of travel.

11. The microfluidic chip of claim 9, wherein an internal geometry of the focusing channel causes the sperm cells to form a focused flow of the sperm cells in the focusing channel.

12. The microfluidic chip of claim 9, wherein the repetitively curved segment comprises one or more symmetrically shaped segments and one or more asymmetrically shaped segments.

13. The microfluidic chip of claim 9, wherein the focusing channel comprises a taper.

14. The microfluidic chip of claim 13, wherein the taper comprises a horizontal or lateral tapering.

15. The microfluidic chip of claim 13, wherein the taper comprises a vertical taper.

16. The microfluidic chip of claim 9, further comprising a detection region.

17. The microfluidic chip of claim 9, further comprising a kill zone.

18. A microfluidic chip for focusing a flow of sperm cells suspended in a fluid, the sperm cells having a diameter (a), the microfluidic chip comprising:
  one or more substrates;
  a focusing channel formed in the one or more substrates and spanning a length from an inlet to an outlet for receiving the flow of sperm cells suspended in the fluid, the focusing channel comprising a repetitively curved segment having a hydraulic diameter ($D_h$), wherein:
    a ratio of the cell diameter to the hydraulic diameter of the channel ($a/D_h$) is between about 0.03 and about 0.06;
    a ratio of curvature (critical parameter "r") to the hydraulic diameter ($D_h$) defined by the formula $2ra^2/D_h^3$ is less than about 0.03; and
  a secondary region comprising a secondary input downstream of the repetitively curved segment.

19. The microfluidic chip of claim 18, wherein the secondary region provides for the adjustment of a position of the flow of sperm cells suspended in the fluid in the focusing channel.

20. The microfluidic chip of claim 18, wherein an internal geometry of the focusing channel causes the sperm cells to form a focused flow of the sperm cells in the focusing channel.

21. The microfluidic chip of claim 18, wherein the repetitively curved segment comprises one or more symmetrically shaped segments and one or more asymmetrically shaped segments.

22. The microfluidic chip of claim 18, wherein the focusing channel comprises a taper.

23. The microfluidic chip of claim 22, wherein the taper comprises a horizontal or lateral tapering.

24. The microfluidic chip of claim 22, wherein the taper comprises a vertical taper.

25. The microfluidic chip of claim 18, further comprising a detection region.

26. The microfluidic chip of claim 18, further comprising a kill zone.

\* \* \* \* \*